US010663963B2

(12) United States Patent
Tuukkanen et al.

(10) Patent No.: US 10,663,963 B2
(45) Date of Patent: May 26, 2020

(54) METHOD AND APPARATUS FOR VISUALIZING FUTURE EVENTS FOR PASSENGERS OF AUTONOMOUS VEHICLES

(71) Applicant: HERE GLOBAL B.V., Eindhoven (NL)

(72) Inventors: Marko Tuukkanen, Schlenzer (DE); Jerome Beaurepaire, Berlin (DE)

(73) Assignee: HERE GLOBAL B.V., Eindhoven (NL)

( * ) Notice: Subject to any disclaimer, the term of this patent is extended or adjusted under 35 U.S.C. 154(b) by 0 days.

(21) Appl. No.: 16/054,752

(22) Filed: Aug. 3, 2018

(65) Prior Publication Data
US 2020/0041997 A1 Feb. 6, 2020

(51) Int. Cl.
G05D 1/00 (2006.01)
B60W 50/14 (2020.01)
B60W 30/095 (2012.01)
G06K 9/00 (2006.01)
A61B 5/18 (2006.01)
B60W 50/00 (2006.01)

(52) U.S. Cl.
CPC ............ G05D 1/0044 (2013.01); A61B 5/18 (2013.01); B60W 30/0953 (2013.01); B60W 30/0956 (2013.01); B60W 50/14 (2013.01); G05D 1/0061 (2013.01); G05D 1/0088 (2013.01); G06K 9/00845 (2013.01); B60W 2050/0028 (2013.01); B60W 2050/146 (2013.01); B60W 2540/22 (2013.01); G05D 2201/0213 (2013.01)

(58) Field of Classification Search
CPC . A61B 5/18; B60W 30/0953; B60W 30/0956; B60W 50/14; B60W 2050/0028; B60W 2050/146; B60W 2540/22; G05D 1/0044; G05D 1/0061; G05D 1/0088; G05D 2201/0213; G06K 9/00845
USPC .......................................................... 701/23
See application file for complete search history.

(56) References Cited

U.S. PATENT DOCUMENTS

| 8,346,426 | B1 | 1/2013 | Szybalski et al. |
| 8,457,827 | B1 | 6/2013 | Ferguson et al. |
| 8,924,150 | B2 | 12/2014 | Tsimhoni et al. |
| 9,008,890 | B1* | 4/2015 | Herbach ................ G01C 21/34 701/26 |
| 9,567,008 | B2 | 2/2017 | Eichhorn |
| 9,772,626 | B2 | 9/2017 | Bendewald et al. |
| 10,105,841 | B1* | 10/2018 | Szatmary ............... B25J 9/1602 |

(Continued)

OTHER PUBLICATIONS

Dey, "Communication of Intention in Autonomous Vehicles", retrieved on Aug. 3, 2018 from https://hci.sbg.ac.at/wp-content/uploads/2016/05/Dey.pdf, 4 pages.

Primary Examiner — Atul Trivedi
(74) Attorney, Agent, or Firm — Ditthavong & Steiner P.C.

(57) ABSTRACT

An approach is provided for visualizing future events to a passenger of a vehicle. The approach involves collecting sensor data, contextual data, or a combination thereof during an operation of a vehicle. The approach also involves processing the sensor data, the contextual data, or a combination thereof to predict a future event that is expected to occur proximate to the vehicle. The approach further involves generating a simulation of the future event. The approach further involves presenting the simulation in a user interface.

20 Claims, 18 Drawing Sheets

(56) References Cited

U.S. PATENT DOCUMENTS

| | | | |
|---|---|---|---|
| 10,514,462 B2* | 12/2019 | Englard | G01S 7/417 |
| 2015/0149088 A1 | 5/2015 | Attard et al. | |
| 2016/0001781 A1* | 1/2016 | Fung | B60R 25/25 |
| | | | 701/36 |
| 2016/0261425 A1* | 9/2016 | Horton | H04L 12/2816 |
| 2017/0008521 A1* | 1/2017 | Braunstein | G01C 21/165 |
| 2017/0024877 A1* | 1/2017 | Versace | G06K 9/00664 |
| 2017/0123421 A1* | 5/2017 | Kentley | G01S 17/87 |
| 2017/0123422 A1* | 5/2017 | Kentley | B60H 1/00735 |
| 2017/0126810 A1* | 5/2017 | Kentley | H04L 67/125 |
| 2017/0132934 A1* | 5/2017 | Kentley | G08G 1/202 |
| 2017/0371347 A1* | 12/2017 | Cohen | G06T 7/73 |
| 2018/0011954 A1* | 1/2018 | Micks | G06F 17/5009 |
| 2018/0032082 A1* | 2/2018 | Shalev-Shwartz | |
| | | | B60W 30/0953 |
| 2018/0101177 A1* | 4/2018 | Cohen | G06K 9/00805 |
| 2018/0113455 A1* | 4/2018 | Iagnemma | B60W 30/00 |
| 2018/0113457 A1* | 4/2018 | Iagnemma | H04W 4/70 |
| 2018/0113463 A1* | 4/2018 | Iagnemma | G05D 1/0061 |
| 2018/0113470 A1* | 4/2018 | Iagnemma | G05D 1/0088 |
| 2018/0117446 A1* | 5/2018 | Tran | A63B 21/0724 |
| 2018/0120859 A1* | 5/2018 | Eagelberg | G05D 1/0088 |
| 2018/0136651 A1* | 5/2018 | Levinson | B60W 30/00 |
| 2019/0047584 A1* | 2/2019 | Donnelly | G06F 3/04842 |
| 2019/0072965 A1* | 3/2019 | Zhang | G05D 1/0212 |
| 2019/0072966 A1* | 3/2019 | Zhang | G05D 1/0212 |
| 2019/0113927 A1* | 4/2019 | Englard | G05D 1/0231 |
| 2019/0155292 A1* | 5/2019 | Gutmann | G05D 1/0223 |
| 2019/0180502 A1* | 6/2019 | Englard | G01S 17/023 |
| 2019/0339688 A1* | 11/2019 | Cella | G06K 9/6263 |

* cited by examiner

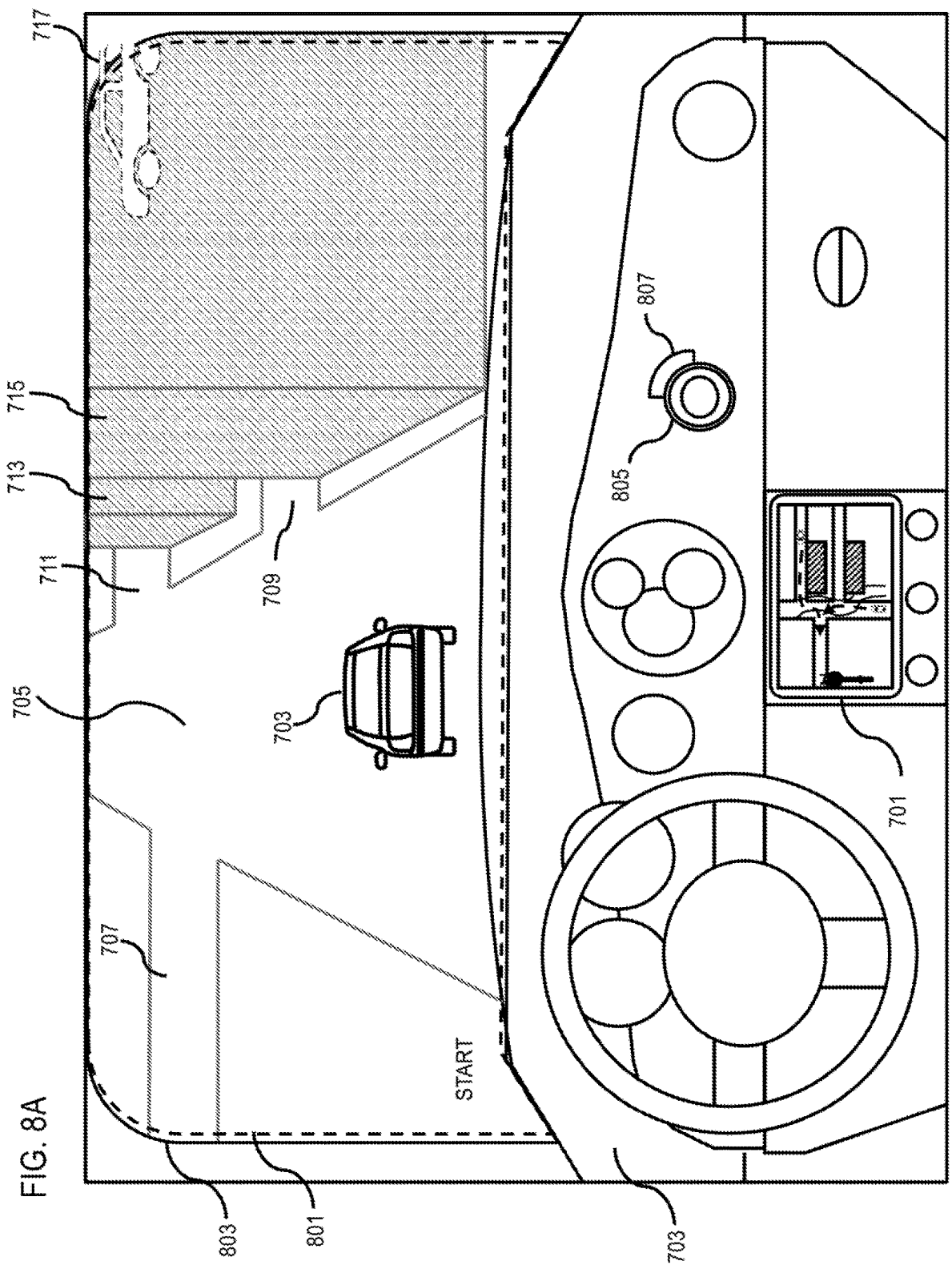

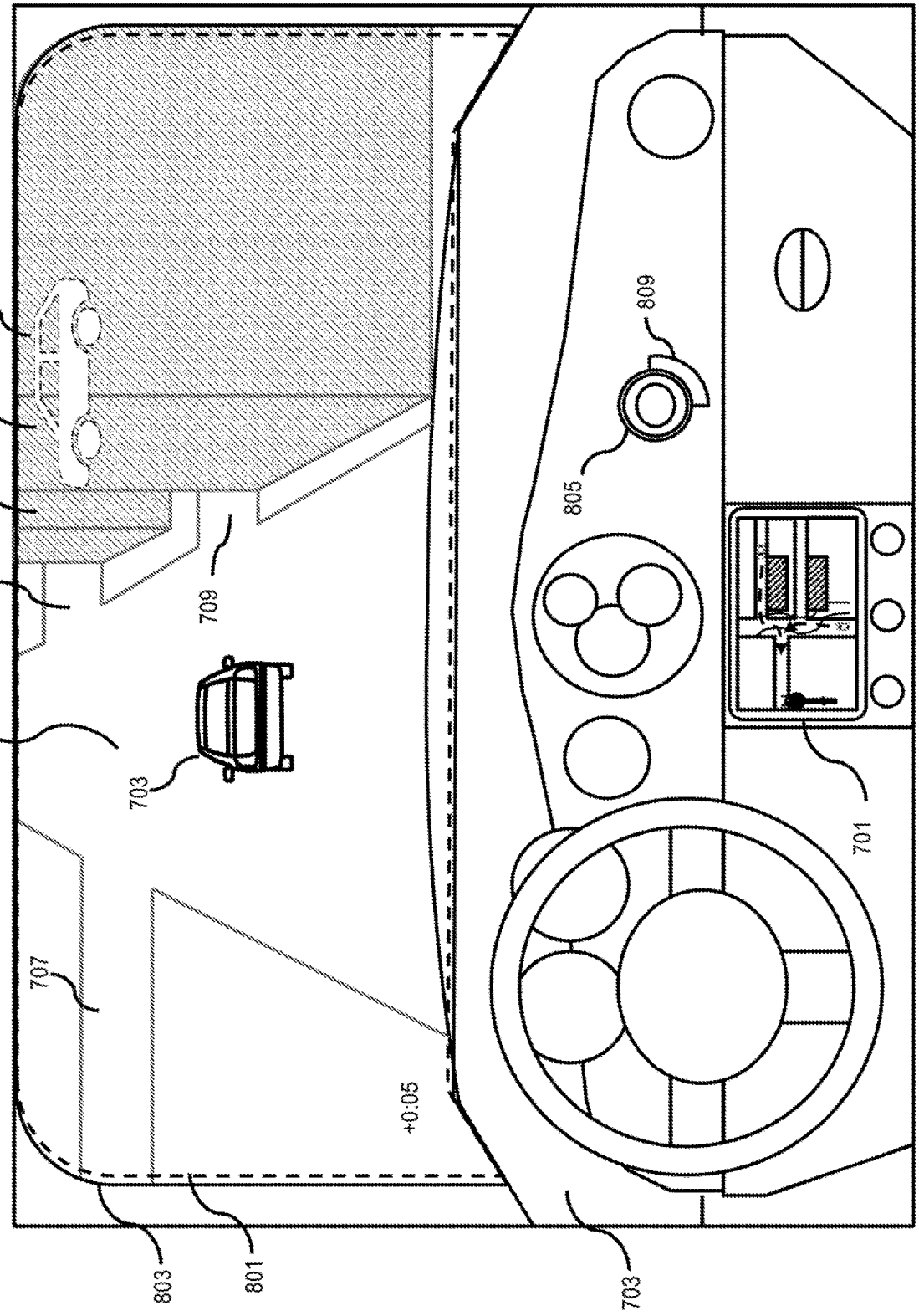

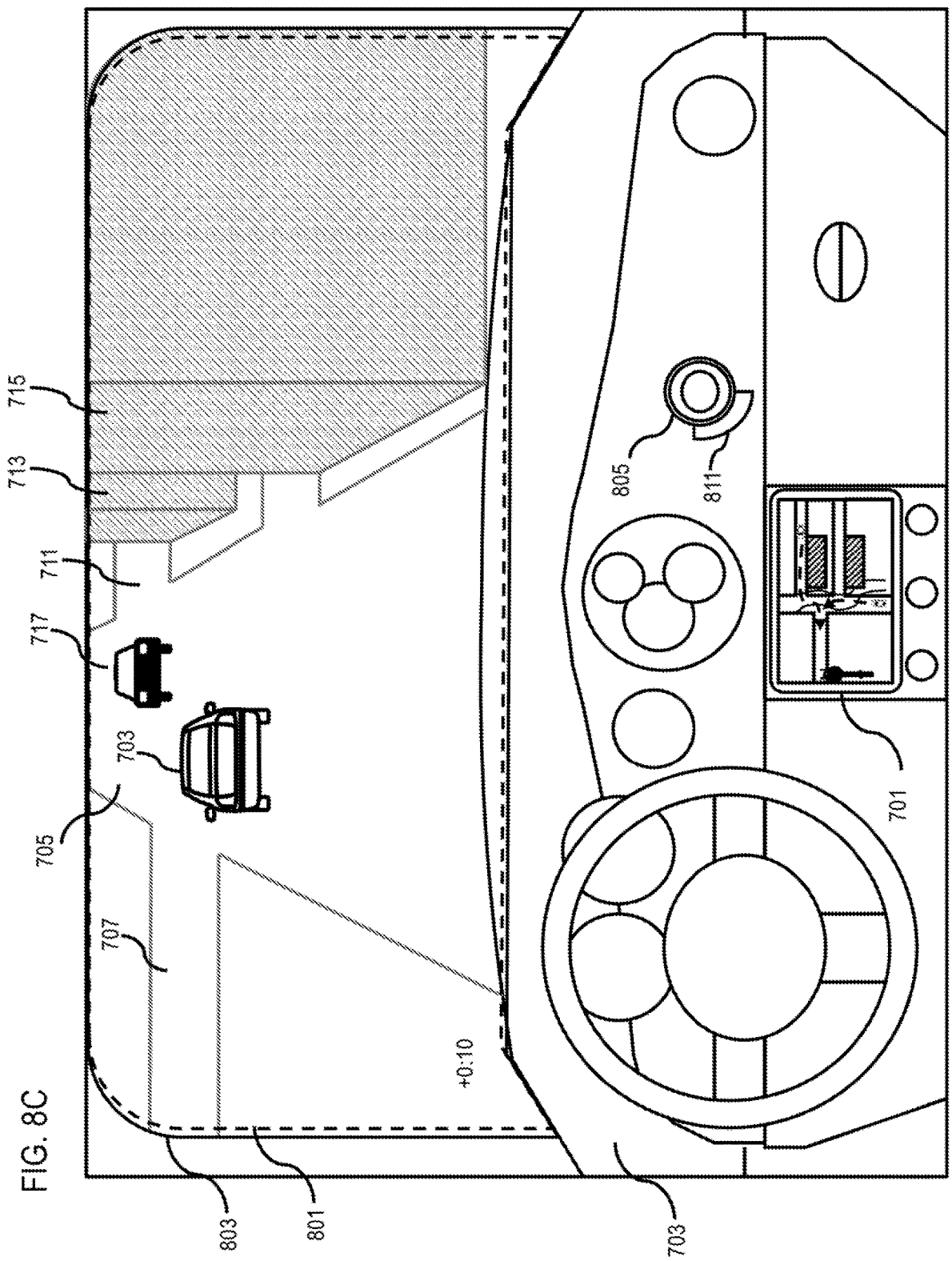

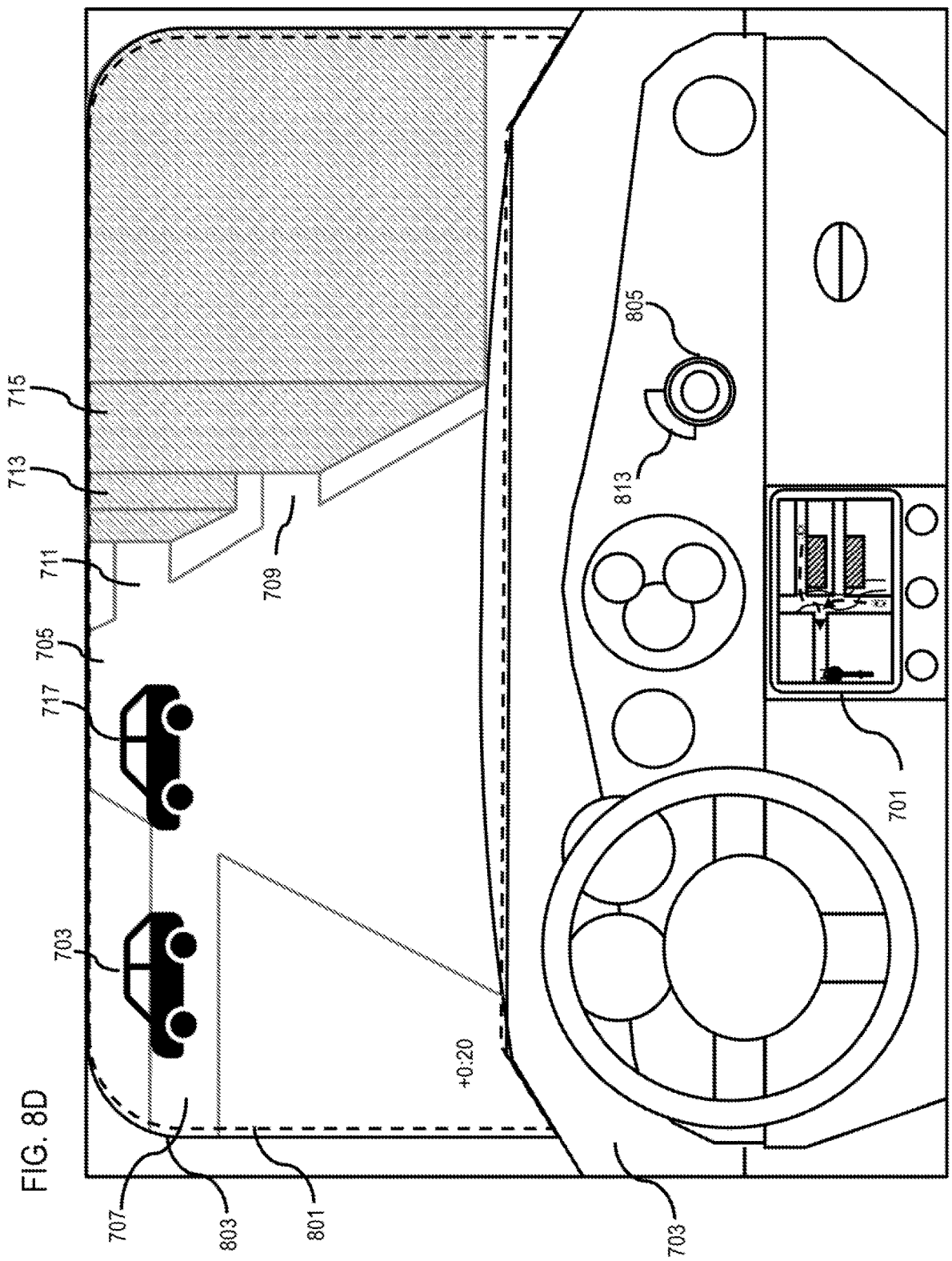

METHOD AND APPARATUS FOR VISUALIZING FUTURE EVENTS FOR PASSENGERS OF AUTONOMOUS VEHICLES

BACKGROUND

Autonomous vehicles are able to operate by using pattern based learning and by processing data from sensors and other sources to support logical decision making (i.e., calculating the probabilities of various scenarios and future events). However, passengers of such vehicles may experience discomfort when the vehicle is being operated by a computer due to the loss of control (e.g., in the same way regular drivers often feel discomfort when they are in a vehicle that is driven by someone else). Further, passengers of autonomous vehicles can become uncomfortable and/or behave unexpectedly when they anticipate or imagine a potential threat (e.g., when they see a vehicle approaching and expect it to cross the path or route of the vehicle that they are in). The feeling of a lack of control often intensifies the unexpected behavior of the passengers (e.g., behavior such as attempting to take manual control in situations where there is no actual danger of collision). Accordingly, service providers face significant technical challenges to minimize the discomfort and unexpected behavior of passengers in autonomous vehicles.

SOME EXAMPLE EMBODIMENTS

As a result, there is a need for visualizing predicted future events (e.g., vehicle position relative to other vehicles or map features) to passengers of autonomous vehicles.

According to one embodiment, a computer-implemented method comprises collecting sensor data, contextual data, or a combination thereof during an operation of a vehicle. The method also comprises processing the sensor data, the contextual data, or a combination thereof to predict a future event that is expected to occur proximate to the vehicle. The method further comprises generating a simulation of the future event. The method further comprises presenting the simulation in a user interface.

According to another embodiment, an apparatus comprises at least one processor, and at least one memory including computer program code for one or more computer programs, the at least one memory and the computer program code configured to, with the at least one processor, cause, at least in part, the apparatus to collect sensor data, contextual data, or a combination thereof during an operation of a vehicle. The apparatus is also caused to process the sensor data, the contextual data, or a combination thereof to predict an event that has occurred or is expected to occur proximate to the vehicle. The apparatus is further caused to generate a simulation of the event. The apparatus is further caused to present the simulation in a user interface.

According to another embodiment, a non-transitory computer-readable storage medium carries one or more sequences of one or more instructions which, when executed by one or more processors, cause, at least in part, an apparatus to collect sensor data, contextual data, or a combination thereof during an operation of a vehicle. The apparatus is also caused to process the sensor data, the contextual data, or a combination thereof to predict an event that has occurred or is expected to occur proximate to the vehicle. The apparatus is further caused to generate a simulation of the event. The apparatus is further caused to present the simulation in a user interface.

According to another embodiment, an apparatus comprises means for collecting sensor data, contextual data, or a combination thereof during an operation of a vehicle. The apparatus also comprises means for processing the sensor data, the contextual data, or a combination thereof to predict a future event that is expected to occur proximate to the vehicle. The apparatus further comprises means for generating a simulation of the future event. The apparatus further comprises means for presenting the simulation in a user interface.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of any of the claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIGS. 8A-8D are diagrams of a vehicle user interface depicting a simulated future event that is expected to occur proximate to a vehicle, according to one embodiment;

DESCRIPTION OF SOME EMBODIMENTS

Examples of a method, apparatus, and computer program for visualizing future events to passengers of autonomous vehicles are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1A:
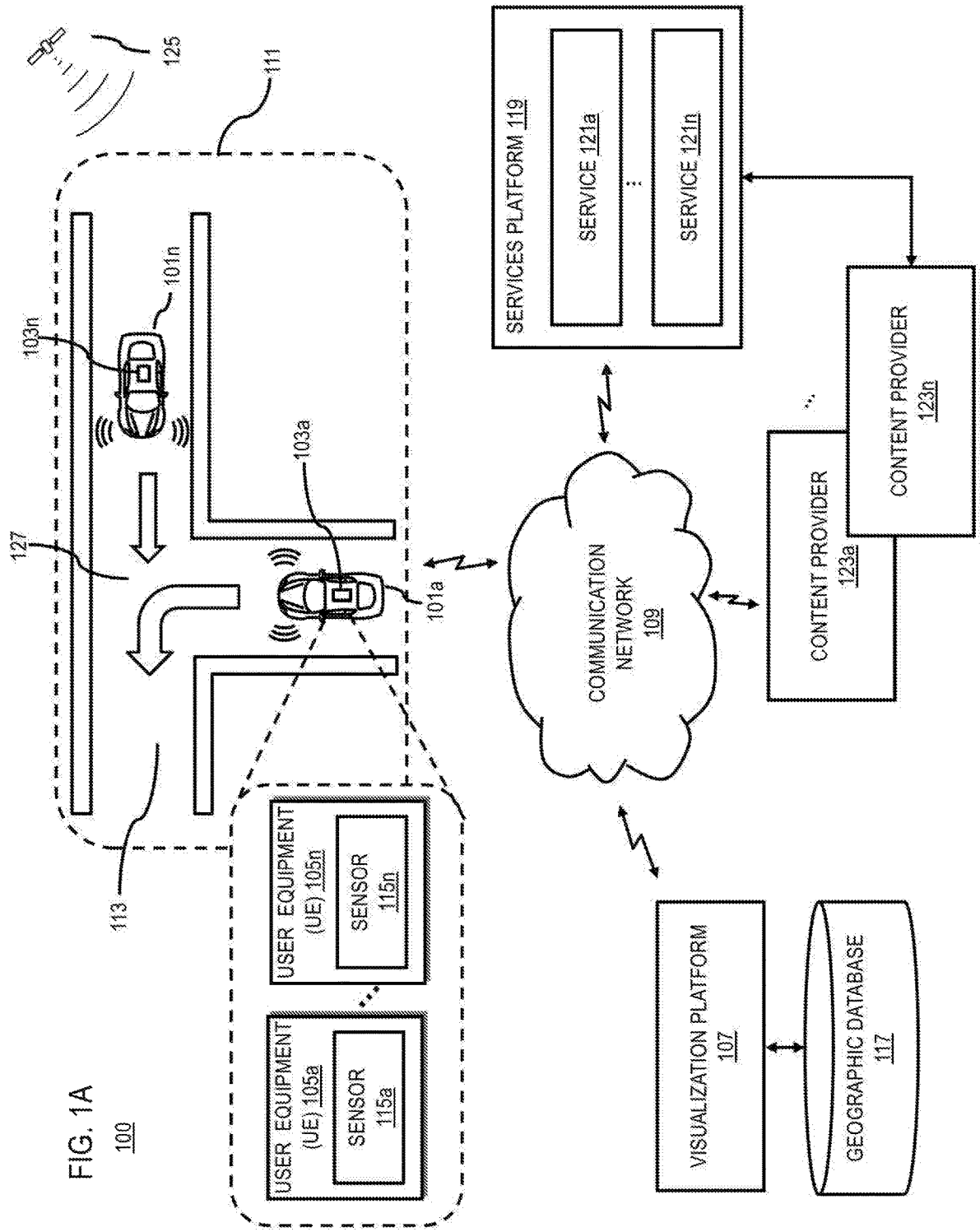
FIG. 1A is a diagram of a system capable of visualizing future events to a passenger of a vehicle, according to one embodiment.

FIG. 1A is a diagram of a system capable of visualizing future events to a passenger of a vehicle (e.g., an autonomous or semi-autonomous car), according to one embodiment. As discussed above, autonomous vehicles can operate using pattern-based learning and by processing data from sensors and other sources to support logical decision making. Although such vehicles can calculate the probabilities of various scenarios and future events, they are still not able to analyze, expect or prepare for unexpected behavior of passengers. Unexpected behavior includes, for instance, behavior that the autonomous vehicle predicts a user should not or need not take given sensed environment parameters (e.g., sensed locations of other nearby vehicles or obstacles). For example, an autonomous vehicle may predict that a gap in traffic is large enough for it to safely merge, make a turn, etc. However, a human passenger may perceive the gap to be too small and become uncomfortable or take manual control of the vehicle to perform a different maneuver (e.g., sudden braking). This type of unexpected behavior can be referred to as illogical or irrational because the autonomous vehicle's control systems predict that the maneuver is safe, and the passenger may be acting out of unfounded fear or discomfort (i.e., expecting the worst) even when the autonomous vehicle knows the planned autonomous maneuver can be performed safely. Moreover, organizations developing such vehicles are not able to reduce the illogical behavior or discomfort that some humans often experience when handing over the control of a vehicle to a computer using traditional approaches.

When it comes to travel, vision is by far the most dominant sense used by most passengers, particularly passengers who are new to autonomous driving. Vision, for instance, enables passengers to observe their surroundings and provide for a sense of anticipation. Anticipation can guide decisions and helps passengers and drivers to prepare for something that has not happened yet. Many people feel discomfort due to the loss of control when inside an autonomous or semi-autonomous vehicle (e.g., a car). These people often behave unexpectedly or irrationally when they anticipate or imagine a potential threat (e.g., an oncoming truck), and the lack of control in the autonomous vehicle intensifies the discomfort or propensity towards irrational behavior of the passenger. This discomfort is like the discomfort that regular drivers often feel when they are in a vehicle driven by someone else, or when they are in an airplane, train, bus, etc. Humans can identify and imagine potential threats and situations that then lead to irrational behavior, even when those threats may not exist.

For example, such a scenario could occur when a passenger sees a vehicle (e.g., a large truck) approaching and she/he expects it to cross the path or route of the vehicle that she/he is riding within. The passenger may believe that the autonomous vehicle is not reacting to the presence of other vehicles or is not reacting quick enough. In such cases, since the vehicle is controlled by the computer, the humans might not have any other options other than to stop the vehicle/computer. However, when passengers anticipate something (e.g., a future event), they are less likely to behave irrationally. For example, when an upcoming or future event is presented to a passenger in an understandable format (i.e., they "see" the future), they can anticipate the event, and be both physically and mentally prepared for the event (i.e., feel comfortable in the autonomous vehicle's decisions or capabilities). Providing such future information in a way that can be quickly and easily perceived by passengers can present significant technical challenges, particularly in dynamic driving or other travel environments that can change quickly.

To address these technical problems, a system 100 of FIG. 1A introduces a capability to visualize future events to a passenger of a vehicle, according to one embodiment. The embodiments of the system 100 described herein, for instance, advantageously enable a presentation of a visual representation of future events, for example, in an augmented reality (AR) or a virtual reality (VR) view inside a vehicle, for example, by projecting the future events into the windows of the vehicle. Such events can include, for example, projecting a second vehicle crossing the path and route of the autonomous vehicle that a passenger is riding within. When passengers inside of the vehicle can see the future event that they are approaching in advance (e.g., in a user interface of a user device, vehicle display, etc.), they can anticipate it and hence their mind will be prepared for the event. The system 100 can enable a passenger of an autonomous vehicle to feel more confident about their autonomous vehicle's decision by means of visualization and by allowing the passengers to experience the upcoming moments on their route before they occur. This presentation of information on future events can help the passenger have a greater sense of anticipation and comfort that the vehicle has also recognized and planned for the same event or events that the passenger has detected visually. The greater comfort can also advantageously result in a decreased likelihood that the passenger will take unexpected actions that would degrade autonomous vehicle performance (e.g., taking inefficient or unwarranted maneuvers that can affect surrounding traffic flow).

In one embodiment, the system 100 can compute future events (e.g., a second vehicle crossing the path and route of the autonomous vehicle, status of a traffic light, etc.) through the aggregation of information coming from other nearby vehicles and objects (e.g., vehicle-to-vehicle (V2V) communications, vehicle-to-infrastructure (V2I), etc.) as well as sensors. By presenting the visual prediction of the future events to a passenger (e.g., the passenger's autonomous vehicle slowing down to give space to another vehicle in the future or stopping for traffic lights), the passenger is provided with a new means for interacting with the autonomous vehicles. By way of example, the system 100 can enable passenger interaction with the route through the visualized future events such as enabling the interaction with the future events (i.e., "play with time"), giving priorities, changing drop off points, etc. This ability can raise a passenger's confidence in and lowering their resistance to autonomous vehicles. By letting a passenger see predictions of most likely future events, the system 100 can reduce the discomfort created by the loss of control and can give a passenger a means to adapt. In one embodiment, the system 100 can present a visualization of the future event within the autonomous vehicle by placing virtual objects in an AR view like the way that virtual navigation arrows can be presented in an AR view on top of a user's lane.

Further, the presentation of the future event to a passenger by the system 100 (e.g., in a safe simulation mode) is helpful because when the passenger(s) inside of the autonomous vehicle can see an event (e.g., a passenger maneuver) or test in advance the future event that they are approaching, they will anticipate it and hence their minds will be "prepared." The system 100, for instance, in addition to providing a visual representation can also provide a passenger with a physical preview of feelings and movements (e.g., the system 100 can move seats in coordination with the prediction of the future event to give the passenger a preview of the movement/feeling from the vehicles point of view). The system 100, for instance, can clearly visually differentiate the current scene form the future events (e.g., through an AR view). In addition, the system 100 can present the system 100's confidence level in the accuracy of a predicted future even (e.g., along a timeline of the future) wherein the further into the future the system 100 looks, the less accurate the prediction may be. The timeline of confidence may be helpful because it is important to understand the psychological limits of each passengers (e.g., how far in the future a passenger normally anticipates and prepares), especially since humans react differently to different events.

In one embodiment, to predict a future event (e.g., a passenger maneuver), the system 100 collects sensor data, contextual data, or a combination thereof during an operation of the passenger's vehicle (e.g., an autonomous or semi-autonomous car). By way of example, the sensor data may be collected using a sensor configured to detect a user's or passenger's gaze, heartrate, sweat rate or perspiration level, eye movement, body movement, or a combination thereof. In one instance, the body movement could include a passenger grabbing her/his seat, double checking the tension of her/his seatbelt, grabbing a handle, bracing against the dashboard, grabbing a front seat if the user in a rear seat, or any other movements passengers may make when they imagine potential threats to the themselves and the vehicle. The contextual data may include, for example, mapping or route information, vehicle-to-everything (V2X) information such as V2V, V2I, etc., passenger location and/or positioning within the autonomous vehicle, object movement information (e.g., static versus moving), status information (e.g., traffic light status, construction status, etc.), time of day, weather conditions, visibility, historical data, etc. In one embodiment, the system 100 collects the sensor data, contextual data, or a combination through one or more sensors such as camera sensors, light sensors, Light Imaging Detection and Ranging (Lidar) sensors, Radio Detection and Ranging (Radar), infrared sensors, thermal sensors, and the like.

In one embodiment, the system 100 processes the sensor data, the contextual data, or a combination thereof to predict a future event that is expected to occur proximate to a vehicle (e.g., an autonomous car). For example, a future event could include when a user sees a vehicle approaching and expects it to cross the path or route of the vehicle that she/he is in, when a user senses that the vehicle will perform a passing maneuver, but it not sure that there is enough space between vehicles, or when a user sees that the vehicle is approaching a complex intersection or interchange (i.e., any events that may cause the passenger to fear or lack confidence in the autonomous vehicle). In one embodiment, the future event includes an autonomous maneuver that the vehicle is predicted to take in response to an object (e.g., a second vehicle or pedestrian), a predicted movement of the object (assuming the object is moving), or a combination thereof. By way of example, the future event may include the autonomous vehicle performing any one of the following actions or maneuvers: overtaking another vehicle; turning at an intersection; turning at or entering a complex intersection or interchange (e.g., a roundabout or an offramp); making a U-turn; parallel parking; or a combination thereof. Similarly, the future event may also include one or more nearby vehicles (e.g., a large truck) performing one or more of the same maneuvers. By way of example, the system 100 can process the data through aggregation, one or more machine learning approaches, filtering area(s) of interest (e.g., field of view, line of sight, on route, distance), or a combination thereof. In one instance, the system 100 can process sensor data, contextual data, or a combination thereof that is within a certain distance to the vehicle (e.g., <100-500 meters). In one instance, the vehicle may be an autonomous car or a semi-autonomous car; however, in another instance, the vehicle could be any means of transportation wherein the passenger is not in control (e.g., an airplane, a train, a ferry, etc.). For example, a future event in this context could include upcoming turbulence that may cause a pilot to rapidly increase or decrease altitude, a sharp turn that will require a train conductor to perform a set of strong braking maneuvers, or a patch of rough or choppy seas prompting a ferry captain to temporarily change course or heading. In each of these examples, the future event may cause a passenger to fear or lack confidence in the operation of the vehicle, particularly where she/he is unable to see what is causing the problem.

In one embodiment, the system 100 predicts the future event for the objects that are proximate to the vehicle (e.g., a second vehicle, a pedestrian, a cyclist, etc.) based on a relevance level of the object to the user of the vehicle. In one embodiment, the relevance level may be determined by the system 100 from sensor data indicating that the user is reacting to or acknowledging the object (e.g., a passenger's heartrate, sweat level, eye movement, grabbing of the seat, etc.) as opposed to reading a book, playing a videogame, or interacting with a personal device. In one instance, the sensor data could include a passenger's interaction with a user interface element (e.g., a joystick) to explicitly select one object (e.g., one specific car of interest looked at by the passenger), several objects (e.g., vehicles on a street/route), all objects within the vehicle's vicinity or scene, or a combination thereof. The determined relevance level is important because the goal of the system 100 is not to force passengers of autonomous vehicles to look at events unless there is a real risk for the safety of the passenger or the passenger requested the visualization (e.g., a passenger interacting with a user interface element such as a knob or trackball-based device). In one instance, the system 100 can compute the future prediction of movement of the most relevant element in a scene (e.g., a vehicle versus a pedestrian or vice-versa). The system 100 may also consider the static or dynamic nature of the object when determining the respective relevance level. For example, traffic lights impact the future, but their locations (and sometimes exact timing) are known. In contrast, the trajectories and speed of moving vehicles are less predictable. Therefore, a presentation of a future event related to a moving object may be more relevant to reducing a passenger's worry or concern. Further, the level of anticipation and discomfort for a given passenger may vary based on the presence of such static or dynamic element(s) in the direct vicinity, the threat they pose for the passenger, and the "urgency" based on time (i.e., how soon the event will take place, 10 seconds versus 45 seconds).

In one embodiment, the system 100 generates a simulation of the future event (e.g., a second vehicle crossing the path and route of the passenger's autonomous vehicle). As described, the future event may include the autonomous vehicle overtaking another vehicle, performing a passing maneuver, turning at an intersection, entering a complex interchange, performing a U-turn, parallel parking, etc. as well as the interactions of other proximate vehicles, pedestrians, cyclists, etc. (i.e., situations where humans can identify and imagine potential threats and situations that then lead to irrational behavior). In one embodiment, the system 100 can simulate the future event by representing the path of a second vehicle over time (e.g., 5 seconds, 10 seconds, 20 seconds, etc.) so that the passenger can physically and mentally anticipate and be prepared for the movement of the second vehicle relative to her/his own vehicle. In one instance, the system 100 can generate a simulation of both vehicles and their respective trajectories to let the passenger know that the two vehicles will, for example, maintain a safe distance from each other despite the passenger's heightened concern (e.g., if the second vehicle is a large or rapidly approaching truck). In one instance, the system 100 can generate a simulation of a path of a nearby pedestrian (e.g., a pedestrian that appears to be about to cross the street ahead of the autonomous vehicle) so that the passenger can know whether the passenger or the pedestrian will be in any danger from the current trajectory of the autonomous vehicle. In one embodiment, the system 100 can generate a safe simulation mode for simulating and testing future events and situations by a passenger (e.g., allowing the passenger to "play with time").

In one embodiment, the system 100 includes a user interface that includes a user interface element configured to receive a user input (e.g., a knob, a joystick, a rollerball or trackball-based interface, a touch screen, etc.) to enable a passenger to specify a parameter of the simulation. In one instance, the system 100 can then generate the simulation based on the one or more specified parameters. By way of example, a parameter can include a time duration (e.g., 5 seconds, 10 seconds, 20 seconds, etc.), a starting time (e.g., a user initiated starting time or a starting time determined by the system 100 based on the one or more sensors), a time direction (e.g., forwards or backwards), starting direction, etc. or a combination thereof. In one embodiment, in addition to or instead of simulating future events, the system 100 can use the embodiments described herein to simulate and playback past events. For example, if a user or passenger feels a sudden braking by the vehicle, the user may request that the system 100 simulate and playback the past event that caused the braking (e.g., another vehicle that suddenly merged in front of the user's vehicle). Following the examples described above, a user on a train, or an airplane, or a boat, for example, that felt a sudden braking, rapid dip or rise in altitude, or unexpected change of course/heading, respectively, could request that the system 100 simulate and playback the past event that caused the braking, the altitude adjustment, change of course, route, heading, etc. In one embodiment, the past simulation can be based on vehicle telemetry data to provide simulations where other traditional means of recording past events (e.g., recorded video) are not available or would consume more system resources (e.g., more memory and processor time for storing and processing video or other image data).

By way of example, the user interface and/or the user interface element could also include in addition to or instead of a knob or roller ball-based interface, a pressure sensor on a screen or window whose intensity reflects the movement of time, an interface that enables gestures/touch interaction, an interface that enables voice commands, pedals or paddles of the autonomous vehicle, or a combination thereof. In one embodiment, the system 100 and the user interface element, e.g., a joystick, enable a passenger to have fun or play a game with the predicted future event. By way of example, the system 100 could track the eyes of a passenger and present the visualized or surfaced future event on each window that a passenger is looking through in real time or substantially real time, thereby creating a 360° immersive view. In one embodiment, the eye-tracking can also be used to determine the specific nearby vehicle, intersection, situation, etc. that the passenger is concerned about. The subject (e.g., vehicle, intersection, etc.) of the user's gaze can then be simulated and visualized by the system 100 according to the various embodiments described herein.

In one embodiment, the system 100 presents the simulation of the future event in a user interface. By way of example, the system 100 can present the simulation in one or more possible rendered views (e.g., two dimensional (2D), three dimensional (3D), AR, VR, etc.) on a window (e.g., a vehicle windshield, a heads-up display, etc.) or in a display (e.g., a handheld display such as a mobile phone or an integrated dashboard or headrest display). In one instance, the user interface could also be a goggle or an eyeglass device used separately or in connection with a mobile device. In one embodiment, the system 100 can present or surface the simulation of the future event in multiple interfaces simultaneously (e.g., presenting a 2D map, a 3D map, an AR view, a VR display, or a combination thereof). In one instance, the system 100 can present the simulation of the future event through multiple interfaces within the vehicle based on the location or positioning of the passengers (e.g., a windshield for passengers in the front seats and on side windows for passengers in the back seats). In one embodiment, the system 100 could also present the simulation of the future event to a passenger through one or more sounds. For example, the system 100 could produce car related sounds (e.g., braking sounds, engine sounds, etc.) or sounds of relevant nearby objects (e.g., a pedestrian talking on a phone), or combination thereof through the speakers of the vehicle. In one embodiment, a user interface (e.g., a car seat) can include a physical actuator to provide a passenger with one or more physical sensations predicted in the simulated future event. By way of example, the system 100 can move a car seat relative to the vehicle's future speed, future road conditions, etc. so that the passenger will better physically and mentally anticipate the event and their bodies and mind will be better "prepared."

In one embodiment, the user interface element (e.g., a knob, a roller or trackball-based interface, etc.) may also be used by a passenger to control the presentation of the of the simulated future event (i.e., play the future). In one instance, a passenger can use the interface element to control and manipulate the visualization of the simulated scene over time (i.e., "playing with the time") by presenting the future in a variety of increments (e.g., 5 second, 10 second, 20 second). In one embodiment, in the scenario where a user has required a projection of 20 seconds ahead, the system 100 can compute and surface this projected future to the user at time t1. As the seconds pass, the "future happens according to the expectations" and the autonomous vehicle happens to be 20 seconds later than where it started (time t2). In this scenario, the system 100 knows that time does not stay still at t1 (time of the original computation). Thus, the system 100 will present the future event in a way that shows that t1 will tend towards t2. In one embodiment, a passenger may also tailor the presentation to her/his interests, for example, presenting only one object (e.g., one specific car of interest); multiple objects (e.g., vehicles on the street or route of the autonomous vehicle); all objects within a certain proximity; for a specific time period of the future; or based on a confidence level of the prediction (i.e., until a threshold value based on time and context is met). In one embodiment, the system 100 or the passenger could organize the presentations in the user interfaces based on a relevance (e.g., more concerning objects/future events being presented on the windshield or a heads-up display and objects/future events of less interest being presented on side windows).

In one embodiment, the system 100 determines a confidence level of the future event (i.e., a confidence level in the prediction), wherein at least one characteristic of a representation of the simulation in the user interface is based on the determined confidence level. By way of example, a car A driving a given route (e.g., known by V2V communication) reaching a location B at time t1 could be represented in a color that suggests confidence or a likelihood of happening (e.g., green). In contrast, if another scenario is less likely to happen due to a variety of possible factors that can impact the generated simulated future event (e.g., traffic), the affected object can be shown in a different way/color suggestive of caution or uncertainty (e.g., yellow). In one instance, the system 100 can present the confidence level of the future event in degrees or intensities of colors, transparency, or a combination thereof such that predicted future events that the system 100 has more confidence in are presented as being less transparent and the predicted future events that the system 100 has less confidence are presented as being more transparent. This visual differentiation can help passengers quickly discern which events to pay attention to and be both physically and mentally prepared for such events. As stated previously, the goal of the system 100 is to avoid presenting simulations of future events to passengers unless there is a real risk for the safety of the passenger. In one embodiment, wherein the predicted future event includes a plurality of potential outcomes, the system 100 can present respective representations of at least two of the plurality of potential outcomes in a user interface (e.g., a heads-up display). By way of example, the system 100 can present one of the future events in a color or a level of transparency and can present the other future event in a different shade, color, or level of intensity such that the passenger can quickly understand which of the plurality of possibilities the system 100 perceives is more likely to occur. The respective representations are particularly advantageous in situations where the object of concern is moving quickly, and the passenger has a short window to decide in terms of her/his anticipation level, fear level, etc.

In one embodiment, after the system 100 visualizes or surfaces a future event to the one or more passengers (e.g., the autonomous vehicle overtaking and passing a vehicle ahead of the autonomous vehicle on the route), the system 100 identifies whether the user acknowledged the event and if any reaction the user had to the visualization, the event, or the combination thereof. By way of example, the system 100 can determine that a user has a fear or a concern about a given situation/intersection/maneuver either implicitly (e.g., through brain reading technology) or explicitly (e.g., line of sight analysis such as recognizing that a user is staring at a car for a few seconds, voice, user interface interaction, physical changes such as increasing heart rate, pulse, adrenaline levels, breathing patterns, etc.). Using this information, the system 100 can better understand the user's worry/concern and build the "projected" view that can help reassure her/him in the decisions of the autonomous vehicle.

In one embodiment, the system 100 determines whether the user acknowledged the future event based on elements detected by the system 100 that hint that the user is worried/concerned about a specific vehicle, intersection, situation, etc. (e.g., heartrate, sweat, eye movements, grabbing the seat, shifting in the seat, bracing for "impact," etc.). In one instance, wherein the system 100 determines that the user either did not see the visualized event (e.g., she/he was reading a book, playing a videogame, interacting with a personal device, etc.) or that the user saw the event and is fine with the event (e.g., there is not a noticeable change in the user's heartrate, eye movement, etc.), no further action is required by the system 100. Again, the goal of the system 100 is not to force passengers of autonomous vehicles to look at events unless there is a real safety risk. In another instance, the system 100 can determine that the user saw the visualized event and had a negative reaction to the simulation (i.e., the user appears concerned). By way of example, the system 100 can determine that the user saw the visualized event and had a negative reaction by a dramatic rise in heartrate, sweat or perspiration levels, eye movement, grabbing the seat, bracing against the dashboard, etc. In one embodiment, the system 100 can generate and present additional visualizations of the simulated future event to try to raise the user's confidence level in the decisions of the autonomous vehicle (e.g., depicting the future event from a different angle). In one embodiment, the system 100 can modify the operation of the vehicle with respect to the future event based on the negative reaction of the user. By way of example, the system 100 can reduce the traveling or turning speeds of the vehicle, reroute the vehicle to avoid complicated intersections or interchanges, avoid certain passing maneuvers based on the user's tolerance, etc. In one embodiment, the system 100 can "recall" that a passenger consistently has a negative reaction to passing large trucks, for example, and can automatically modify the operation of the vehicle or the system 100 can prompt the passenger as to the passenger's past reactions and inquire as to whether the system 100 should continue a previously requested operation and/or present the future even again (e.g., to determine whether the user's tolerance has changed over time due to factors such as familiarity).

In one embodiment, the system 100 can enable the user to modify the operation of the vehicle in response to the future event (e.g., by interacting with the user interface element). By way of example, in a passive mode setting, the system 100 "simply" computes the scene in the given context based on the available information coming from the car(s), the network, the sensors, etc., and aims at surfacing this to the car passengers. However, in an active mode setting, the user would be able to "influence" some of the decisions coming in the next few seconds, respecting of course all limitations and regulations (e.g., speed limits, traffic lights, etc.). By way of example, a user may decide to let a car pass before her/him at some intersection to make her/him feel more comfortable. Given the number of passengers in the example of a plane, train, ferry, etc. the possibility of an active mode may be less likely; however, if the system 100 detected that a majority of the passengers shared the same concern, then the users may be able to collectively influence the operations of a plane, a train, a ferry, etc. much like a single user would influence some of the decisions of an autonomous car. This could be done by a simple interface (e.g., a roller track ball or a mobile device, or a voice command) that helps slowing down the car at a given future location. The system 100's ability to switch between passive and active mode setting recognizes that not all passengers share the same confidence level, tolerance level, or even desire to participate in the decisions of an autonomous vehicle.

As shown in FIG. 1A, the system 100 comprises one or more vehicles 101*a*-101*n* (also collectively referred to herein as vehicles 101) configured with one or more vehicle sensors 103*a*-103*n* (also collectively referred to herein as vehicle sensors 103), one or more user equipment (UE) 105*a*-105*n* (also collectively referred to herein as UEs 105) having connectivity to a visualization platform 107 via a communication network 109. In one embodiment, the vehicles 101 are autonomous vehicles or highly assisted driving vehicles that can sense their environments and navigate within a travel network 111 without driver or occupant input. In one embodiment, one or more passengers are riding within the vehicle 101*a*. Although the vehicles 101 are depicted as automobiles, it is contemplated the vehicle 101 may be an any type of transportation wherein a passenger is not in control (e.g., an airplane, a train, a ferry, etc.). In one embodiment, the vehicle sensors 103 (e.g., camera sensors, light sensors, Lidar sensors, Radar, infrared sensors, thermal sensors, and the like) acquire contextual data during an operation of the vehicle 101 along one or more roads 113 within the travel network 111. By of example, the contextual data may include mapping or route information, V2X information such as V2V, V2I, etc. passenger location and or positioning within the vehicle 101, object movement information (e.g., static versus moving objects) status information (e.g., traffic light status, construction status, etc., time of day, weather conditions, visibility information, historical data, etc.). In one embodiment, the vehicle sensors 103 can determine whether a passenger is grabbing her/his seat, checking the tension of her/his seatbelt, grabbing a handle, pushing against the dashboard (i.e., any physical manifestation on the part of the passenger hinting that she/he is worried/concerned about a specific vehicle/intersection/situation).

In one embodiment, the UEs 105 can be associated with any of the types of vehicles or a person or thing traveling within the travel network 111. By way of example, the UE 105 can be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, fitness device, television receiver, radio broadcast receiver, electronic book device, game device, devices associated with one or more vehicles or any combination thereof, including the accessories and peripherals of these devices, or any combination thereof. It is also contemplated that the UE 105 can support any type of interface to the user (such as "wearable" circuitry, etc.). In one embodiment, the one or more vehicles may have cellular or wireless fidelity (Wi-Fi) connection either through the inbuilt communication equipment or from the UE 105 associated with the vehicles 101. Also, the UEs 105 may be configured to access a communication network 109 by way of any known or still developing communication protocols. In one embodiment, the UEs 105 include a user interface element configured to receive a user input (e.g., a knob, a joystick, a rollerball or trackball-based interface, a touch screen, etc.). In one embodiment, the user interface element could also include a pressure sensor on a screen or a window (e.g., a windshield of a vehicle 101, a heads-up display, etc.) whose intensity reflects the movement of time, an interface element that enables gestures/touch interaction by a user, an interface element that enables voice commands by a user, or a combination thereof. In one embodiment, the UEs 101 may are configured with various passenger sensors 115*a*-115 (also collectively referred to herein as passenger sensors 115) for collecting passenger sensor data during an operation of the vehicle 101 along one or more roads 113 within the travel network 111. By way of example, the passenger sensors 115 are any type of sensor that can detect a passenger's gaze, heartrate, sweat rate or perspiration level, eye movement, body movement, or combination thereof. In one embodiment, the passenger sensors 115 can determine a baseline for each passenger and determine whether a passenger is worried/concerned about a specific vehicle/intersection/situation, etc. (e.g., by determining a dramatic rise or increase in the passenger's heartrate, eye movement, etc.).

In one embodiment, the vehicles 101 also have connectivity to a visualization platform 107 over the communication network 109. In one embodiment, the visualization platform 107 performs the process for visualizing future events to a passenger of a vehicle as discussed with respect to the various embodiments described herein. In one embodiment, the visualization platform 107 can be a cloud-based platform that collects and processes sensor data from sensors 103 and 115, contextual data regarding the passengers and the vehicle 101's surroundings, or a combination thereof. In one embodiment, the visualization platform 107 can be a standalone server or a component of another device with connectivity to the communication network 109. For example, the component can be part of an edge computing network where remote computing devices (not shown) are installed along or within proximity of the travel network 111. In one embodiment, the visualization platform 107 performs functions related to generating mapping data (e.g., location-based records) related to static or moving objects proximate to the vehicle 101 (e.g., vehicles, pedestrians, traffic lights, etc.) and correlates them to geographic areas described in a geographic database 117. In one embodiment, the visualization platform 107 has connectivity over the communication network 109 to the services platform 119 (e.g., an OEM platform) that provides one or more services 121a-121n (also collectively referred to herein as services 121) (e.g., sensor data collection services). By way of example, the services 121 may also be other third-party services and include mapping services, navigation services, travel planning services, notification services, social networking services, content (e.g., audio, video, images, etc.) provisioning services, application services, storage services, contextual information determination services, location-based services, information-based services (e.g., weather, news, etc.), etc.

In one embodiment, content providers 123a-123n (collectively referred to as content providers 123) may provide content or data (e.g., including geographic data, parametric representations of mapped features, historical data, etc.) to the geographic database 117, the visualization platform 107, the services platform 119, the services 121, and the vehicles 101. The content provided may be any type of content, such as map content, contextual content, audio content, video content, image content, etc. In one embodiment, the content providers 123 may also store content associated with the geographic database 117, visualization platform 107, services platform 119, services 121, and/or vehicles 101. In another embodiment, the content providers 123 may manage access to a central repository of data, and offer a consistent, standard interface to data, such as a repository of the geographic database 117.

By way of example, as previously stated the vehicle sensors 103 may be any type of sensor. In certain embodiments, the vehicle sensors 103 may include, for example, a global positioning sensor for gathering location data, a network detection sensor for detecting wireless signals or receivers for different short-range communications (e.g., Bluetooth, Wi-Fi, light fidelity (Li-Fi), near field communication (NFC) etc.), temporal information sensors, a camera/imaging sensor for gathering image data (e.g., for detecting objects proximate to the vehicle 101a), an audio recorder for gathering audio data (e.g., detecting nearby humans or animals via acoustic signatures such as voices or animal noises), velocity sensors, and the like. In another embodiment, the vehicle sensors 103 may include sensors (e.g., mounted along a perimeter of the vehicle 101) to detect the relative distance of the vehicle from lanes or roadways, the presence of other vehicles (e.g., vehicle 101n), pedestrians, animals, traffic lights, road features (e.g., curves) and any other objects, or a combination thereof. In one scenario, the vehicle sensors 103 may detect weather data, traffic information, or a combination thereof. In one example embodiment, the vehicles may include GPS receivers to obtain geographic coordinates from satellites 125 for determining current location and time. Further, the location can be determined by a triangulation system such as A-GPS, Cell of Origin, or other location extrapolation technologies when cellular or network signals are available. In another example embodiment, the one or more vehicle sensors 103 may provide in-vehicle navigation services.

The communication network 109 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (Wi-Fi), wireless LAN (WLAN), Bluetooth®, Internet Protocol (IP) data casting, satellite, mobile ad-hoc network (MANET), and the like, or any combination thereof.

In one embodiment, the visualization platform 107 may be a platform with multiple interconnected components. By way of example, the visualization platform 107 may include multiple servers, intelligent networking devices, computing devices, components and corresponding software for determining future events for one or more locations based, at least in part, on signage information. In addition, it is noted that the visualization platform 107 may be a separate entity of the system 100, a part of the services platform 119, the one or more services 121, or the content providers 123.

In one embodiment, the geographic database 117 stores information on road links (e.g., road length, road breadth, slope information, curvature information, etc.), probe data for one or more road links 113 (e.g., traffic density information), and historical accident data associated the road links 113 or other geographic areas within the travel network 111. The information may be any of multiple types of information that can provide means for triggering vehicle sensor activation based on proximate object detection. In another embodiment, the geographic database 117 may be in a cloud and/or in a vehicle 101 (e.g., an autonomous car) and/or a mobile device (e.g., a UE 105).

By way of example, the vehicles 101, the UEs 105, the visualization platform 107, the services platform 119, and the content providers 123 communicate with each other and other components of the communication network 109 using well known, new or still developing protocols. In this context, a protocol includes a set of rules defining how the network nodes within the communication network 109 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 1B:
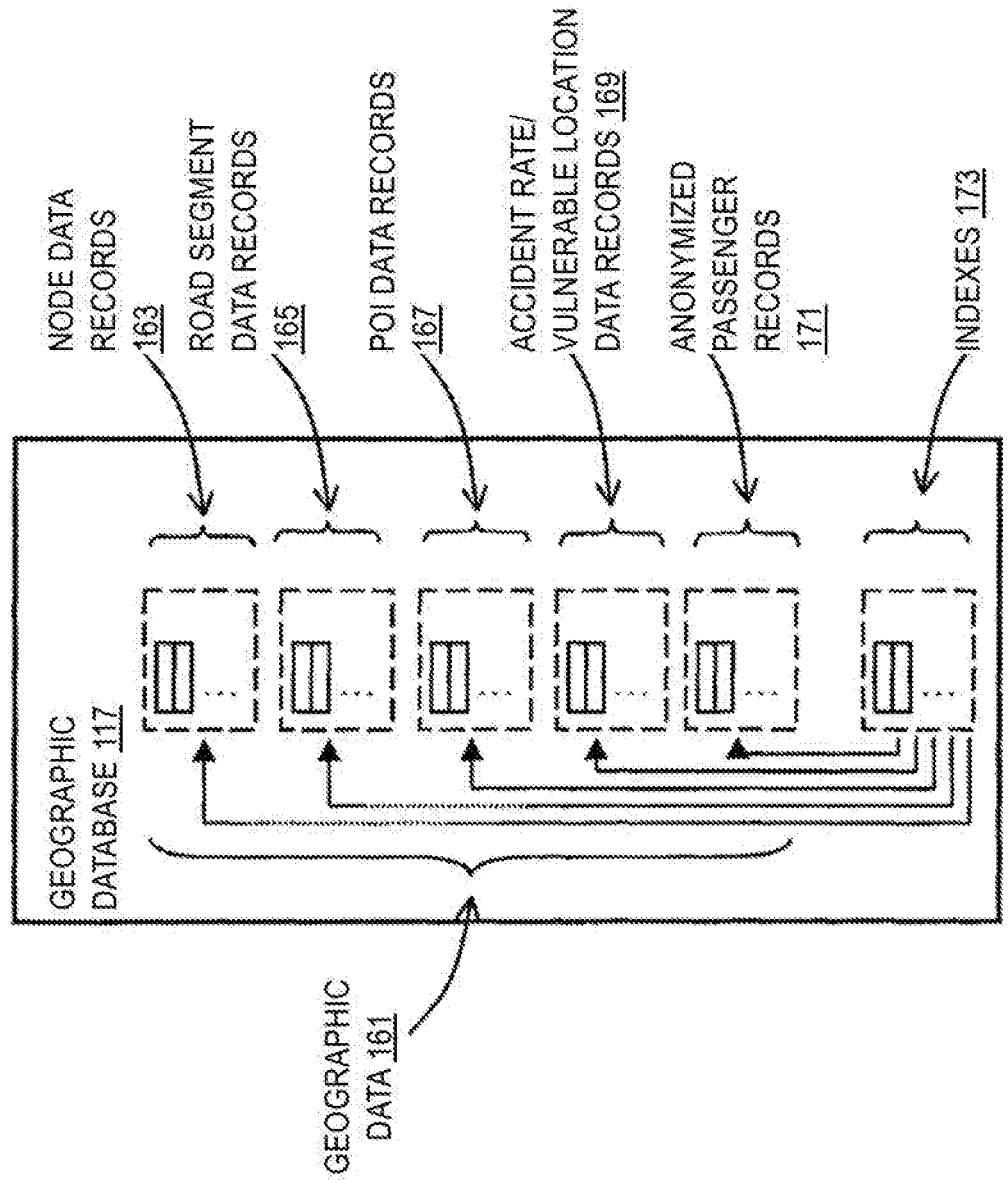
FIG. 1B is a diagram of a geographic database of the system of FIG. 1A, according to one embodiment.

FIG. 1B is a diagram of the geographic database 117 of the system 100, according to exemplary embodiments. In the exemplary embodiments, contextual data, predicted future event data, simulations of future events, relevance data, confidence data, etc. can be stored, associated with, and/or linked to the geographic database 117 or data thereof. In one embodiment, the geographic or map database 117 includes geographic data 161 used for (or configured to be compiled to be used for) mapping and/or navigation-related services, such as for location-based triggering of vehicle sensors 103 as discussed in the various embodiments described herein. The geographic data 161 can also be used for personalized route determination, according to exemplary embodiments. For example, the geographic database 117 includes node data records 163, road segment or link data records 165, POI data records 167, accident rate/vulnerable location records 169, anonymized passenger records 171, and indexes 173 for example. More, fewer or different data records can be provided. In one embodiment, the additional data records (not shown) can include cartographic ("carto") data records, routing data, and maneuver data. In one embodiment, the indexes 173 may improve the speed of data retrieval operations in the geographic database 117. For example, the indexes 173 may be used to quickly locate data without having to search every row in the geographic database 117 every time it is accessed.

In exemplary embodiments, the road segment data records 165 are links or segments representing roads (e.g., road 113 of the travel network 111), streets, parking areas, or paths, as can be used in the calculated route or recorded route information for determination of one or more personalized routes, according to exemplary embodiments. The node data records 163 are end points corresponding to the respective links or segments of the road segment data records 165. The road link data records 165 and the node data records 163 represent a road network or travel network 111, such as used by vehicles, cars, and/or other entities. Alternatively, the geographic database 117 can contain path segment and node data records or other data that represent pedestrian paths or areas in addition to or instead of the vehicle road record data, for example.

The road link and nodes can be associated with attributes, such as geographic coordinates, street names, address ranges, speed limits, turn restrictions at intersections, and other navigation related attributes, as well as POIs, such as gasoline stations, hotels, restaurants, museums, stadiums, offices, automobile dealerships, auto repair shops, buildings, stores, parks, parking areas (attributes on which parking areas are critical) etc. The geographic database 117 can include data about the POIs and their respective locations in the POI data records 167. The geographic database 117 can also include data about places, such as cities, towns, or other communities, and other geographic features, such as bodies of water, mountain ranges, etc. Such place or feature data can be part of the POI data 167 or can be associated with POIs or POI data records 167 (such as a data point used for displaying or representing a position of a city).

In one embodiment, the geographic database 117 also includes accident rate/vulnerable location data records 169. For example, data records 169 may specify an accident rate associated with the links or nodes of the geographic data 161. The accident rate can be further specified by mode of transport (e.g., vehicle, pedestrian, etc.). In this way, the accident rate/vulnerable location data records 169 can provide information on vehicle accident rates occurring at a location (e.g., intersection 127 of FIG. 1A). In addition, the data records 169 can indicate whether a link or node of the geographic data includes any locations that are vulnerable road user locations (e.g., a complicated intersection) that is likely to cause a passenger worry or concern and therefore the system 100 may present the predicted future event to the passenger sooner than later in the approach.

In one embodiment, the geographic database 117 also includes anonymized passenger records 171. By way of example, anonymized passenger records 171 may include information to suggest that a particular route of the vehicle 101 is familiar to the passenger and therefore the passenger has more confidence in the vehicle 101's decisions. In one embodiment, the anonymized passenger records 171 can be used by the system 100 to determine a threshold, an interest, or a relevance of proximate objects to a passenger (e.g., if the passenger is a child or an experienced driver).

The geographic database 117 can be maintained by the content provider 123 in association with the services platform 119 (e.g., a map developer). The map developer can collect geographic data to generate and enhance the geographic database 117. There can be different ways used by the map developer to collect data. These ways can include obtaining data from other sources, such as municipalities or respective geographic authorities (e.g., designated parking areas). In addition, the map developer can employ field personnel to travel by vehicle along roads throughout the geographic region to observe features and/or record information about them, for example. Also, remote sensing, such as aerial or satellite photography, can be used.

The geographic database 117 can be a master geographic database stored in a format that facilitates updating, maintenance, and development. For example, the master geographic database 117 or data in the master geographic database 117 can be in an Oracle spatial format or other spatial format, such as for development or production purposes. The Oracle spatial format or development/production database can be compiled into a delivery format, such as a geographic data files (GDF) format. The data in the production and/or delivery formats can be compiled or further compiled to form geographic database products or databases, which can be used in end user navigation devices or systems.

For example, geographic data is compiled (such as into a platform specification format (PSF) format) to organize and/or configure the data for performing navigation-related functions and/or services, such as route calculation, route guidance, map display, speed calculation, distance and travel time functions, and other functions, by a navigation device, such as a navigation system of the vehicle 101, for example. The navigation-related functions can correspond to vehicle navigation, pedestrian navigation, or other types of navigation. The compilation to produce the end user databases can be performed by a party or entity separate from the map developer. For example, a customer of the map developer, such as a navigation device developer or other end user device developer, can perform compilation on a received geographic database in a delivery format to produce one or more compiled navigation databases.

As mentioned above, the geographic database 117 can be a master geographic database, but in alternate embodiments, the geographic database 117 can represent a compiled navigation database that can be used in or with end user devices (e.g., vehicles 101, UEs 105) to provide navigation-related functions or location-based functions (e.g., triggering vehicle sensor activation based on objects such as a second vehicle crossing the path and route of the vehicle 101a). For example, the geographic database 117 can be used with the vehicle 101 to provide an end user with navigation features. In such a case, the geographic database 117 can be downloaded or stored in a navigation system of the vehicle 101, or the vehicle 101 can access the geographic database 117 through a data connection over the communication network 109, for example.

Figure 2:
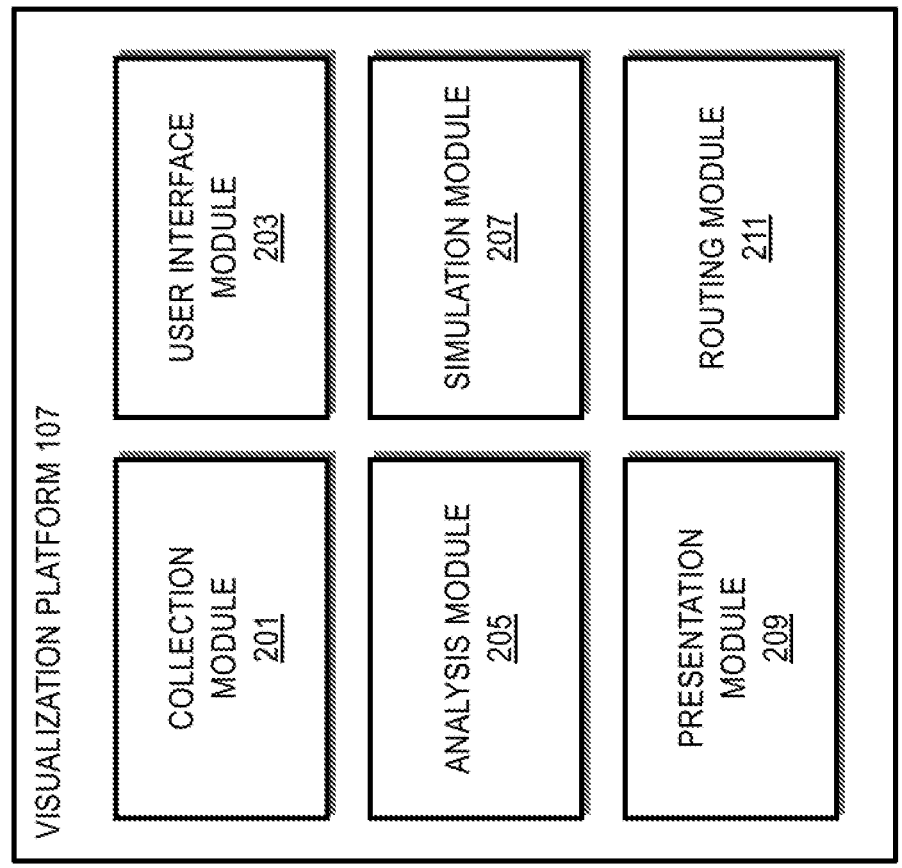
FIG. 2 is a diagram of the components of a visualization platform, according to one embodiment.

FIG. 2 is a diagram of the components of a visualization platform 107, according to one embodiment. By way of example, the visualization platform 107 includes one or more components for visualizing future events to a passenger of a vehicle (e.g., an autonomous vehicle). It is contemplated that the functions of these components may be combined in one or more components or performed by other components of equivalent functionality. In one embodiment, the visualization platform 107 includes a collection module 201, a user interface (UI) module 203, an analysis module 205, a simulation module 207, a presentation module 209, and a routing module 211. The above presented modules and components of the visualization platform 107 can be implemented in hardware, firmware, software, or a combination thereof. Though depicted as a separate entity in FIG. 1A, it is contemplated that the visualization platform 107 may be implemented as a module of any of the components of the system 100. In another embodiment, the visualization platform 107 and/or one or more of the modules 201-211 may be implemented as a cloud-based service, local service, native application, or combination thereof. The functions of the visualization platform 107 and the modules 201-211 are discussed with respect to FIGS. 3-6 below.

Figure 3:
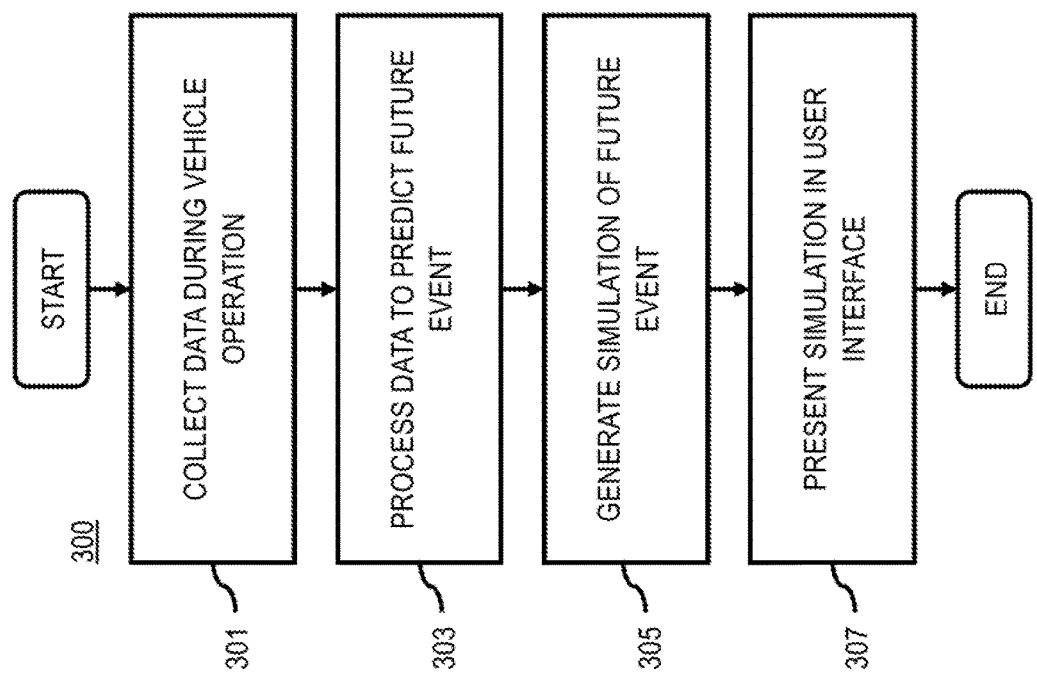
FIG. 3 is a flowchart of a process for visualizing future events to a passenger of a vehicle, according to one embodiment.
Figure 10:
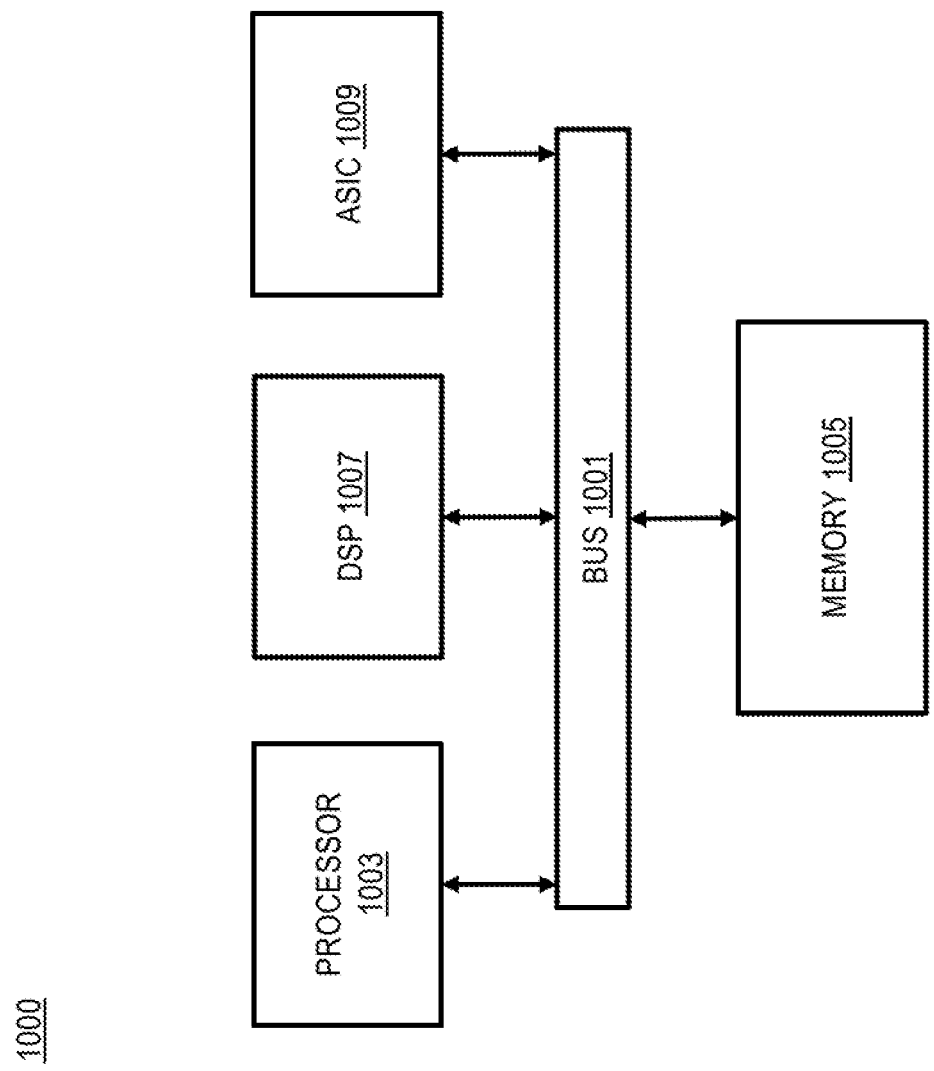
FIG. 10 is a diagram of a chip set that can be used to implement an embodiment of the invention.

FIG. 3 is a flowchart of a process for visualizing a future event to a passenger of a vehicle, according to one embodiment. In various embodiments, the visualization platform 107 and/or the modules 201-211 of the visualization platform 107 as shown in FIG. 2 may perform one or more portions of the process 300 and may be implement in, for instance, a chip set including a processor and a memory as shown in FIG. 10. As such, the visualization platform 107 and/or the modules 201-211 can provide means for accomplishing various parts of the process 300, as well as means for accomplishing embodiments of other processes described herein in conjunction with other components of the system 100. Although the process 300 is illustrated and described as a sequence of steps, it is contemplated that various embodiments of the process 300 may be performed in any order or combination and need not include all of the illustrated steps.

In step 301, the collection module 201 collects sensor data, contextual data, or a combination thereof during an operation of a vehicle. By way of example, the vehicle (e.g., a vehicle 101) may be an autonomous or semi-autonomous vehicle (e.g., a car). In one embodiment, the vehicle could be any means of transportation where a passenger is not in control (e.g., an airplane, a train, a ferry, etc.). In one instance, the sensor data may be collected by the collection module 201 and the user interface module 203 using a sensor configured to detect a user's or a passenger's gaze, heartrate, sweat rate or perspiration level, eye movement, body movement, or a combination thereof. By way of example, the sensor and/or user interface module 203 could consist of brain reading technology, a blood pressure cuff, a fingertip pulse oximeter and heart rate monitor, an eye tracking device, or a combination thereof. In one embodiment, the collection module 201 could determine that a passenger is grabbing her/his seat, double checking the tension of her/his seatbelt, pushing against the dashboard or any other movement suggesting that the passenger is worried/concerned about a vehicle/intersection/situation. In one embodiment, the collection module 201 collects the contextual data via one or more vehicle sensors 103 (e.g., camera sensors, light sensors, Lidar sensors, Radar, infrared sensors, thermal sensors, and the like). By way of example, the contextual data may include mapping or route information, V2X information such as V2V, V2I, etc. passenger location and/or positioning with the vehicle (e.g., the vehicle 101a), object movement information (e.g., static versus moving), status information (e.g., traffic light status), time of day, weather conditions, visibility, historical data, etc.

In step 303, the analysis module 205 processes the sensor data, the contextual data, or a combination thereof to predict a future event that is expected to occur proximate to a vehicle. As described above, anticipation guides our decisions and, therefore, preparing passengers physically and mentally for something that hasn't happened yet is important to reduce a passenger's discomfort created by a loss of control. By way of example, a future event could include when a user sees a vehicle (e.g., vehicle 101n) approaching and expects it to cross the path or route of her/his own vehicle (e.g., vehicle 101a), which may cause the passenger to fear or lack confidence in the vehicle 101. In one instance, the future event may include an autonomous maneuver that the vehicle (e.g., vehicle 101a) is predicted to take in response to an object (e.g., a vehicle 101n, a pedestrian stepping into the road, etc.), a predicted movement of an object (e.g., the vehicle 101n), or a combination thereof. For example, the future event may include the vehicles 101 performing any of the following actions of maneuvers: overtaking another vehicle; turning at an intersection; turning at or entering a complex intersection or interchange (e.g., a roundabout or an offramp), making a U-turn, parallel parking, or a combination thereof. In one embodiment, the analysis module 205 processes the sensor data, the contextual data, or a combination thereof through aggregation, one or more machine learning approaches, category filtering (e.g., field of view, line of sight, on route, distance, etc.), or a combination thereof. In one embodiment, the analysis module 205 can process sensor data, contextual data, or a combination thereof that is within a certain distance to a vehicle 101 (e.g., <100-500 meters).

In step 305, the simulation module 207 generates a simulation of the future event. In one use case, the future event may be a second vehicle (e.g., vehicle 101n) crossing the path and route of the vehicle 101a (e.g., an autonomous vehicle that a passenger is riding within). By way of example, the simulation module 207, in connection with the analysis module 205, can simulate the future event by representing the path of the second vehicle over time (e.g., 5 seconds, 10 seconds, 20 seconds, etc.) so that the passenger can physically and mentally anticipate (i.e., be prepared for) the movement of the second vehicle relative to her/his own vehicle. In one instance, the simulation module 207 can generate a simulation showing the passenger a movement of the second vehicle that is currently not within the passenger's field of view or line of sight (e.g., blocked by a building ahead). In one embodiment, the simulation module 207 can generate a simulation of both vehicles (e.g., vehicle 101a and 101n) and their respective trajectories to let the passenger know, e.g., that the two vehicles will maintain a safe distance from each other despite the passenger's fear (e.g., if the second vehicle is a large truck). By way of example, the simulation module 207 can also generate a simulation of a path of a nearby pedestrian (e.g., a pedestrian that looks like she/he is about to cross the street or path ahead of the passenger's vehicle) to inform that passenger whether the passenger or the pedestrian are in any true danger from the maneuvers of the vehicle 101. In one embodiment, the simulation module 207 can generate a safe simulation mode to enable a passenger to simulate and test future events and situations (i.e., enabling a passenger to "play with time").

In step 307, the presentation module 209 presents the simulation in a user interface. By way of example, the user interface can include any type of UE 105 (e.g., a mobile device or an in-dash navigation display). In one embodiment, the interface includes a user interface element configured to receive a user input (e.g., a knob, a joystick, a rollerball or trackball-based interface, a touch screen, etc.) to enable a passenger to specify a parameter or the simulation. In one instance, the user interface could comprise a pressure sensor on a screen or a window (e.g., a vehicle windshield or heads-up display) whose intensity reflects the movement of time, an interface that enables gestures/touch interaction, an interface that enables voice commands, pedals or paddles of a vehicle (e.g., the vehicle 101a). In one embodiment, the presentation module 209 can present the simulation to a passenger in one or more possible rendered views (e.g., 2D, 3D, AR, VR, etc.). In one embodiment, the presentation module 209 can present one or more rendered views on a window (e.g., a windshield or heads-up display of a vehicle 101) or in a display (e.g., a handheld display or an integrated dashboard or headrest display). In one instance, the presentation module 209, in connection with the user interface module 203, could present the simulation to the passenger through a goggle or eyeglass-based device used separately or in connection with a mobile device (e.g., a UE 105). In one embodiment, the presentation module 209 can present or surface the simulation of the future event in multiple interfaces simultaneously (e.g., presenting an AR view on a windshield and a 2D map in a display). In one instance, the presentation module 209, in connection with the collection module 201 and the UI module 203, can present the simulation through multiple interfaces within the vehicle (e.g., vehicle 101a) based on the location or positioning of the passengers (e.g., a windshield for passengers in the front seats and on side windows for passengers in the back seats). In one embodiment, the presentation module 209 can present the simulation through one or more sounds. By way of example, the presentation module 209 could produce car related sounds (e.g., braking, accelerating, etc.) or sounds of relevant nearby objects (e.g., a pedestrian talking on a phone), or a combination thereof through the speakers of the vehicle 101. In one instance, the presentation module 209 can also present the simulation to the passenger through one or more physical sensations predicted in the simulated future event (e.g., moving a car seat relative to the vehicle's future speed, future road conditions, etc.).

The above presented modules 201-211 and components of the visualization platform 107 can be implemented in hardware, firmware, software, or a combination thereof.

Figure 4:
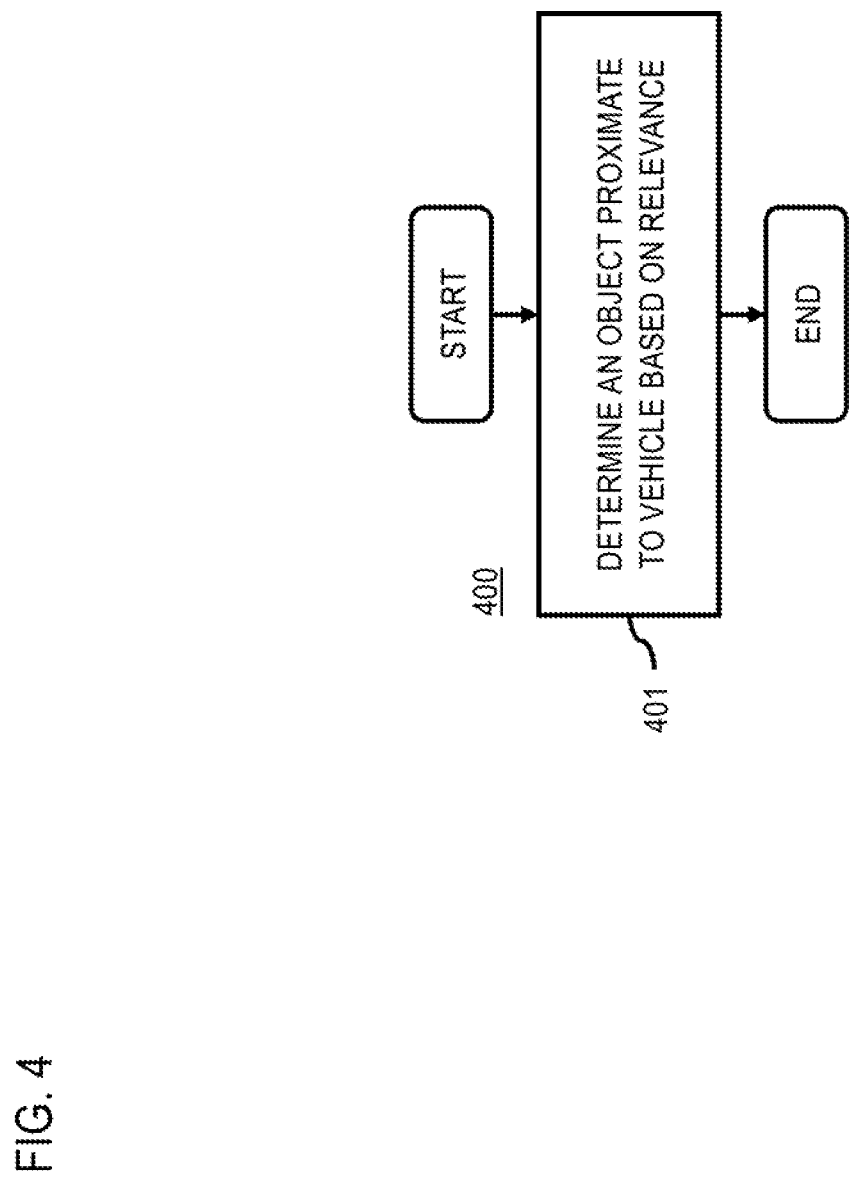
FIG. 4 is a flowchart of a process for predicting a future event that is expected to occur proximate to a vehicle, according to one embodiment.

FIG. 4 is a flowchart of a process for predicting a future event that is expected to occur proximate to a vehicle, according to one embodiment. In various embodiments, the visualization platform 107 and/or the modules 201-211 of the visualization platform 107 as shown in FIG. 2 may perform one or more portions of the process 400 and may be implement in, for instance, a chip set including a processor and a memory as shown in FIG. 10. As such, the visualization platform 107 and/or the modules 201-211 can provide means for accomplishing various parts of the process 400, as well as means for accomplishing embodiments of other processes described herein in conjunction with other components of the system 100. Although the process 400 is illustrated and described as a sequence of steps, it is contemplated that various embodiments of the process 400 may be performed in any order or combination and need not include all of the illustrated steps.

In step 401, the analysis module 205 determines an object proximate to the vehicle based on a relevance level of the object to a user of the vehicle, wherein the future event is predicted with respect to the object. By way of example, the object may be a vehicle 101 (e.g., the vehicle 101n) crossing the path and route of the passenger's vehicle (e.g., an autonomous vehicle or the vehicle 101a). In one instance, the object may also be a pedestrian (e.g., a pedestrian crossing the path and route of the passenger's vehicle). For example, the object may be in the line of sight of the passenger or the object may be obscured (e.g., behind a building). In one embodiment, the analysis module 205 determines the relevance level of the object (e.g., an oncoming vehicle), in connection with the collection module 201, based on sensor data (e.g., heartrate, sweat level, eye moving, grabbing of a seat, etc.) indicating that a passenger is reacting to the object. In one instance, the analysis module 205 could determine the relevance level, in connection with the user interface module 203, based on a passenger's interaction with a user interface element (e.g., a joystick) to explicitly select an object (e.g., one specific car of interest looked at by the passenger), several objects (e.g., vehicles 101 on a street/route), all objects within the vehicle 101's vicinity or scene, or a combination thereof. In one embodiment, the analysis module 205 can determine the relevance level of the object (e.g., vehicle 101n), in connection with the collection module 201, based on whether the object is static or moving.

Figure 5:
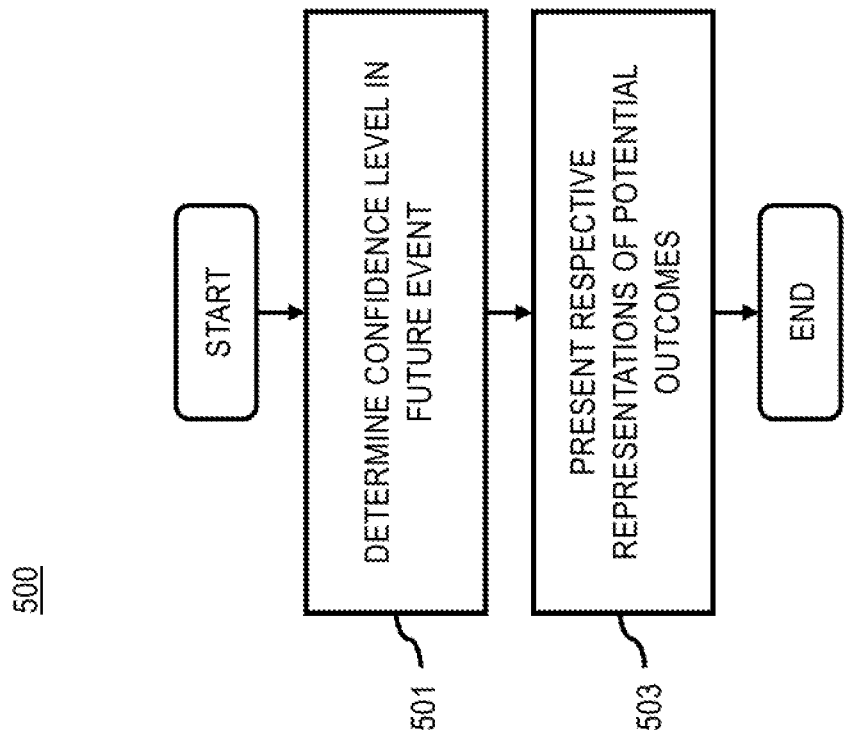
FIG. 5 is a flowchart of a process for presenting a simulation of a future event in a user interface, according to one embodiment.

FIG. 5 is a flowchart of a process for presenting a simulation of a future event in a user interface, according to one embodiment. In various embodiments, the visualization platform 107 and/or the modules 201-211 of the visualization platform 107 as shown in FIG. 2 may perform one or more portions of the process 500 and may be implement in, for instance, a chip set including a processor and a memory as shown in FIG. 10. As such, the visualization platform 107 and/or the modules 201-211 can provide means for accomplishing various parts of the process 500, as well as means for accomplishing embodiments of other processes described herein in conjunction with other components of the system 100. Although the process 500 is illustrated and described as a sequence of steps, it is contemplated that various embodiments of the process 500 may be performed in any order or combination and need not include all of the illustrated steps.

In step 501, the analysis module 205 determines a confidence level of the future event, wherein at least one characteristic of a representation of the simulation in the user interface is based on the confidence level. By way of example, the confidence level may be based on whether the future event includes a static or a moving object. For example, traffic lights impact the future, but their locations (and sometimes exact timing) are known. In contrast, the trajectories and speed of moving vehicles 101 are less predictable, particularly if driven by a human versus being an autonomous vehicle. Similarly, the analysis module 205 could have confidence in the belief that a car A driving a given route (e.g., known by V2V communication) with little or no other objects in the vicinity will likely reach location B at time t1. In contrast, the analysis module 205 may not have the same confidence level if there are number of other objects (e.g., traffic) or obstacles (e.g., construction) that could easily delay the car A from reaching location B at time t1. In one embodiment, the presentation module 209 presents the simulation in the user interface based on the confidence level. By way of example, the at least one characteristic of a representation could include a color, a transparency level, or a combination thereof reflecting the confidence that the analysis module 205 has in the future event related to an object (e.g., representing a static vehicle in green and an oncoming vehicle in red or yellow). In one instance, the presentation module 209 can present the confidence level of the analysis module 205 in the future event in degrees of intensities of colors, transparency, or a combination thereof such that predicted future events that the analysis module 205 has more confidence in (e.g., based on voluminous data) are presented as being less transparent and the predicted future events that the analysis module 205 has less confidence can be presented by the presentation module 209 as being more transparent.

In step 503, wherein the future event includes a plurality of potential outcomes, the presentation module 209 presents respective representations of at least two of the plurality of potential outcomes in the user interface. By way of example, the presentation module 209 can present one of the future events in a color or a level of transparency and can present the other future event in a different shade or level of intensity such that the passenger can quickly discern which of the possibilities the analysis module 205 has more confidence in and/or is more likely to occur.

Figure 6:
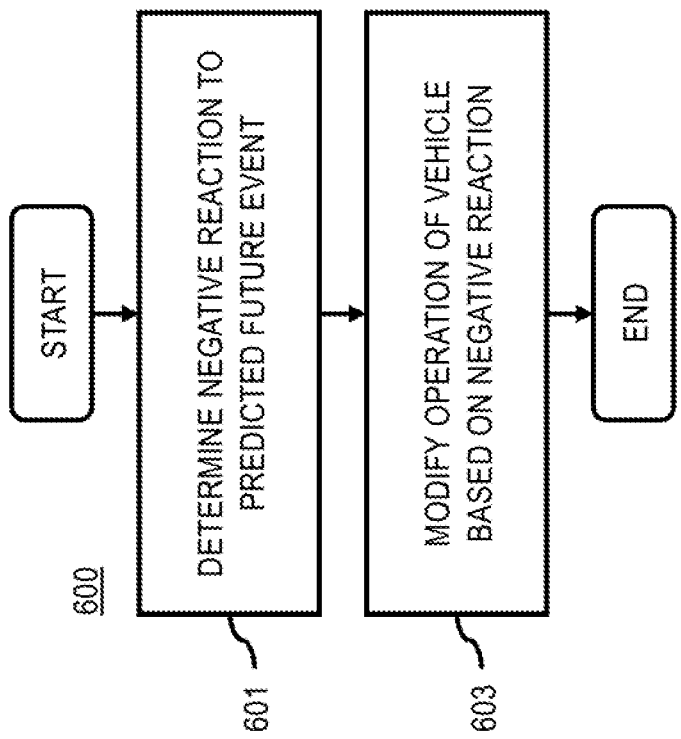
FIG. 6 is a flowchart of a process for modifying an operation of a vehicle based on a passenger's reaction to a presentation of a future event, according to one embodiment.

FIG. 6 is a flowchart of a process for modifying an operation of a vehicle based on a passenger's reaction to a presentation of a future event, according to one embodiment. In various embodiments, the visualization platform 107 and/or the modules 201-211 of the visualization platform 107 as shown in FIG. 2 may perform one or more portions of the process 600 and may be implement in, for instance, a chip set including a processor and a memory as shown in FIG. 10. As such, the visualization platform 107 and/or the modules 201-211 can provide means for accomplishing various parts of the process 600, as well as means for accomplishing embodiments of other processes described herein in conjunction with other components of the system 100. Although the process 600 is illustrated and described as a sequence of steps, it is contemplated that various embodiments of the process 600 may be performed in any order or combination and need not include all of the illustrated steps.

In step 601, the collection module 201 determines a negative reaction of the user to the simulation of the future event. By way of example, the collection module 201 can determine a negative reaction based on a dramatic rise in a passenger's heartrate, sweat or perspiration levels, eye movement, grabbing a seat, bracing against a dashboard, or a combination thereof. In one instance, the negative reaction suggests that the passenger has worry/concern about a specific vehicle/intersection/situation. In one use case, the simulated future event may be the passenger's vehicle 101 (e.g., an autonomous car) overtaking and passing a large truck. Although the presentation module 209 show the passenger that her/his vehicle can overtake and pass the large truck without problem, the passenger may still have worry/concern or even fear that the vehicle will not make the pass successfully.

In step 603, the routing module 211 modifies the operation of the vehicle with respect to the future event based on the negative reaction. By way of example, the routing module 211 can reduce the traveling or turning speeds of the vehicle 101, reroute the vehicle 101 to avoid complicated intersections or interchanges, avoid certain passing maneuvers as discussed in the use case above, or a combination thereof based on the reactions of the passenger. In one embodiment, the routing module 211 may already be aware of a passenger's tolerance or confidence in such actions or maneuvers and can prompt the passenger through the user interface module 203 to determine whether the routing module 211 should modify the operation based on a previous negative reaction or whether the routing module 211 should wait to see what if any reaction the passenger has to a new simulation of a future event.

FIGS. 7A-7D are diagrams of a map user interface depicting a simulated future event that is expected to occur proximate to a vehicle, according to one embodiment. As shown, the map user interface 701 of FIGS. 7A-7D (e.g., a UE 105 such as a mobile device) depicts a presentation of a future event over time t1 (FIG. 7A), t2 (FIG. 7B), t3 (FIG. 7C), and t4 (FIG. 7D), by the visualization platform 107 to one or more passengers of the vehicle 703 (e.g., an autonomous car). In one embodiment, the visualization platform 107 first collects sensor data, contextual data, or a combination thereof during an operation of the vehicle 703. In this use case, at t1 (start), the vehicle 703 is heading north on road 705. In one embodiment, the visualization platform 107 can determine that a passenger in the front seat of the vehicle 703 is worried/concerned about an upcoming left turn from road 705 to road 707 since she/he knows from experience that roads 709 and 711 both feed into road 707 through road 705 and she/he can see that buildings 713 and 715 block her/his view of traffic traveling west of the roads 709 and 711, respectively. In this instance, the visualization platform 107 determines that the front seat passenger is concerned based on the determined increase in the passenger's heartrate and sweat rate. In one embodiment, in addition to collecting sensor data relative to the front seat passenger, the visualization platform 107 also collects contextual data such as V2V information indicating that a second vehicle (e.g., vehicle 717) is heading west on road 711 and its navigation system informs the visualization platform 107 that it will be turning south on road 705 and then west on road 707 at or about the same time that the vehicle 703 is turning west on road 707.

In one embodiment, the visualization platform 107 processes the sensor data, the contextual data, or a combination thereof to predict a future event that is expected to occur proximate to the vehicle 703. In this instance, the visualization platform 107 can determine from the contextual data of the vehicle 703 and the vehicle 717 (e.g., V2V information) that although both vehicles will be face-to-face at t3 (FIG. 7C), there is sufficient time for the vehicle 703 to make its turn west on road 707 at t4 (FIG. 7D) before vehicle 717 is even ready to make its turn west on road 707 (i.e., there is no real risk to the safety of the passenger).

In one embodiment, once the visualization platform 107 processes the sensor data, the contextual data, or a combination thereof, the visualization platform 107 can generate a simulation of the predicted future event. In this instance, the visualization platform can simulate the future event by simulating the paths of the vehicles 703 and 717 over the times t1, t2, t3, and t4 (e.g., 3:00, 3:05, 3:10, 3:20) as depicted in FIGS. 7A-7D, respectively.

In one embodiment, once the visualization platform 107 generates the simulation of the future event (e.g., vehicles 703 and 717 turning onto road 707), the visualization platform 107 can present the simulation in the user interfaces 701 of FIGS. 7A-7D. By way of example, the visualization platform 107 can present the future event in one or more possible rendered views (e.g., a 2D map, a 3D map, an AR view, or a VR view). In this instance, at t1, the visualization platform 107 may not have that much confidence in its predicted future event given the fact that the vehicle 717 is a moving object and appears to be driven by a human versus being another autonomous vehicle. Consequently, the visualization platform 107 may represent the vehicle 717 in manner suggestive of caution (e.g., with a high level of transparency and/or in a yellow color). In contrast, the visualization platform 107 may represent the road 709 in a manner suggestive of confidence or certainty (e.g., a green color) at t1 (FIG. 7A) to show the front seat passenger that at t1, the visualization platform 107 has a high degree of confidence in the fact that there are no incoming vehicles for the passenger to worry about. As time passes and the visualization platform 107 collects and processes more contextual data, the visualization platform 107's confidence level regarding its predicted future event should increase and the visualization platform 107 can adjust its representation of the vehicle 717 (e.g., decreasing the level of transparency and/or changing the color from yellow to green as time passes between t1, t2, t3, and t4 (FIGS. 7A-7D, respectively). Similarly, as time passes, the visualization platform 107 may lose confidence in its predicted future event regarding road 709 (e.g., a vehicle 719 not present at t1 may appear at t4). Therefore, the visualization platform 107 can adjust its representation of road 709 over the course of time (e.g., green to red in FIGS. 7A-7D, respectively).

Figure 7A:
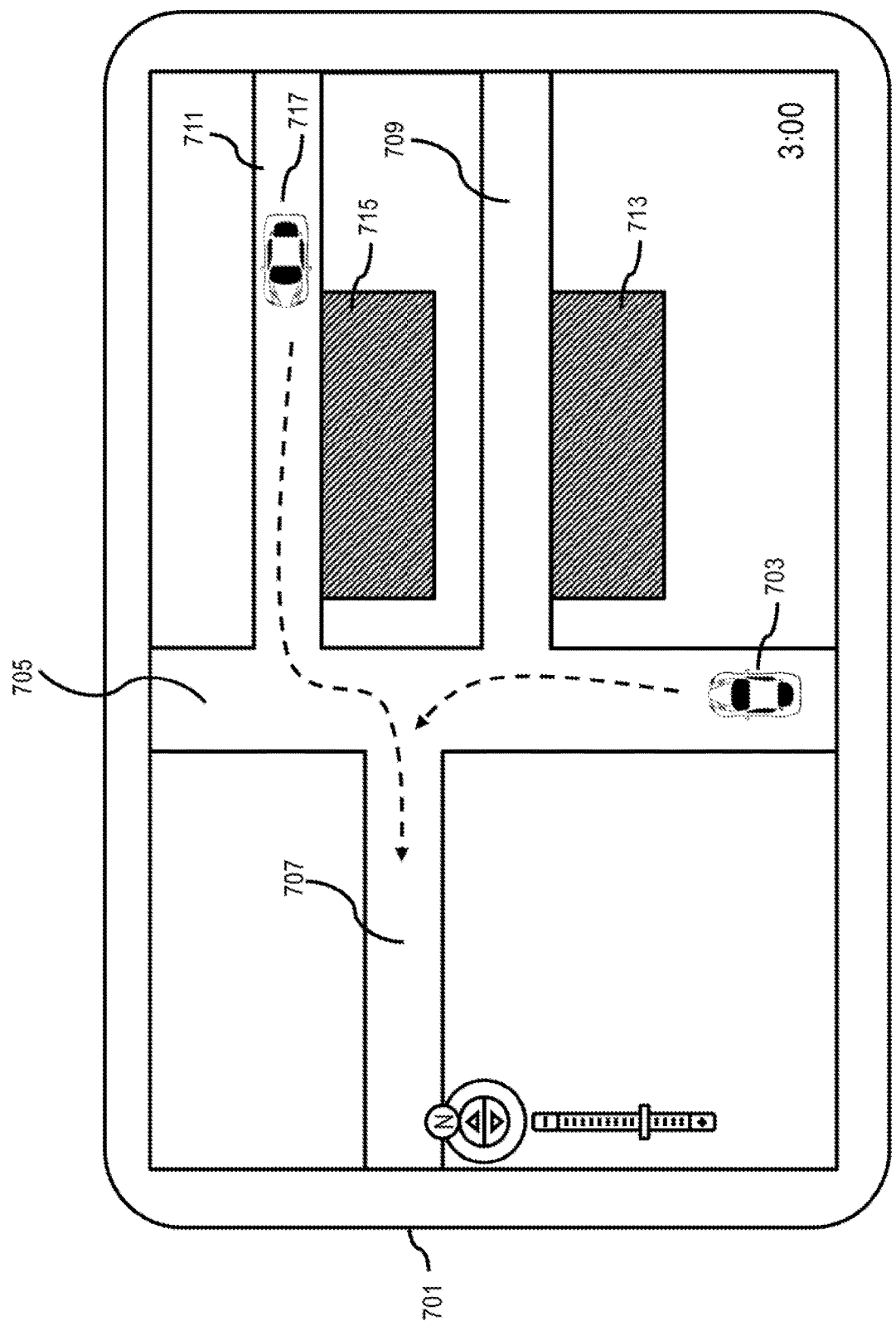
FIGS. 7A-7D are diagrams of a map user interface depicting a simulated future event that is expected to occur proximate to a vehicle, according to one embodiment.
Figure 7B:
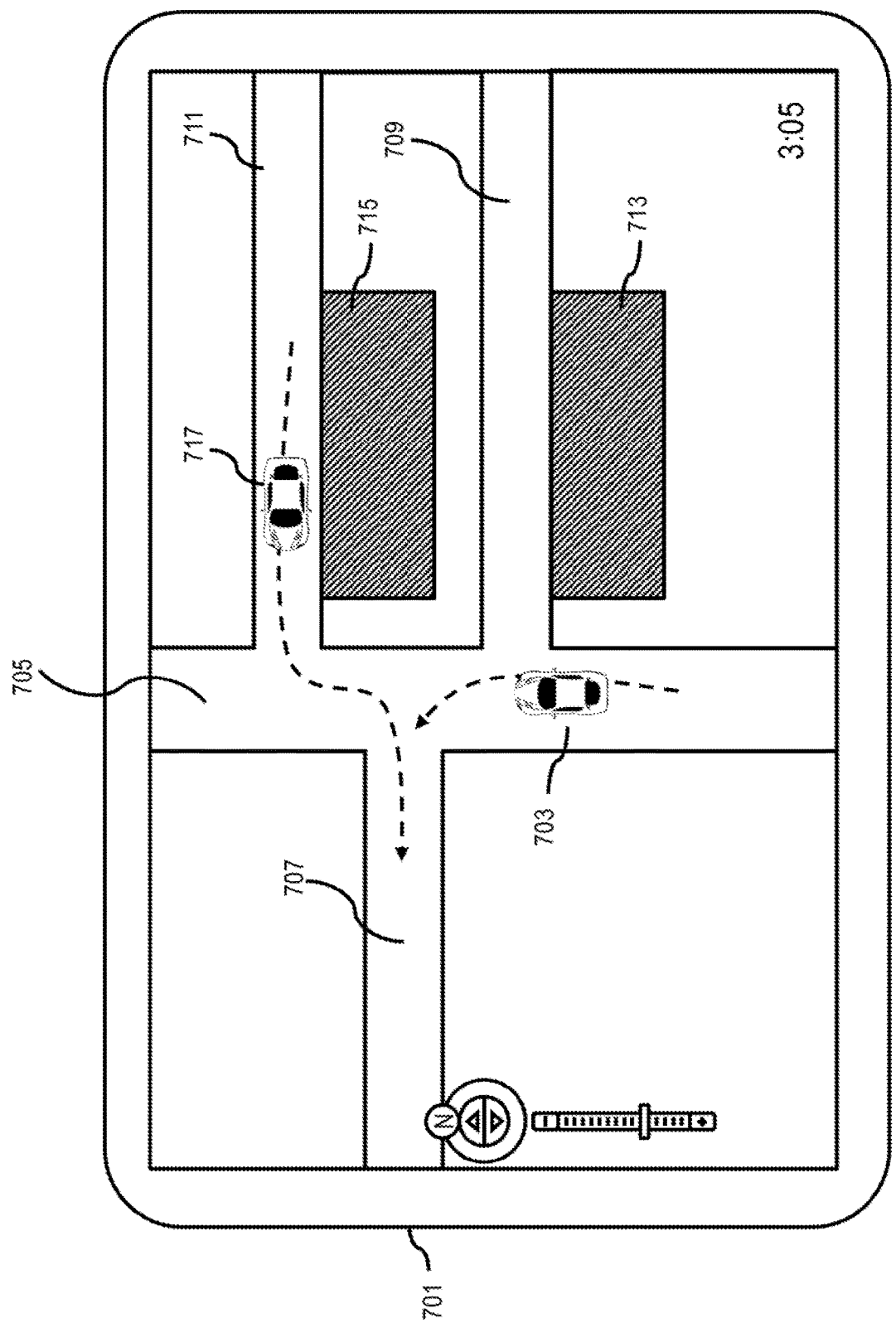
Figure 7C:
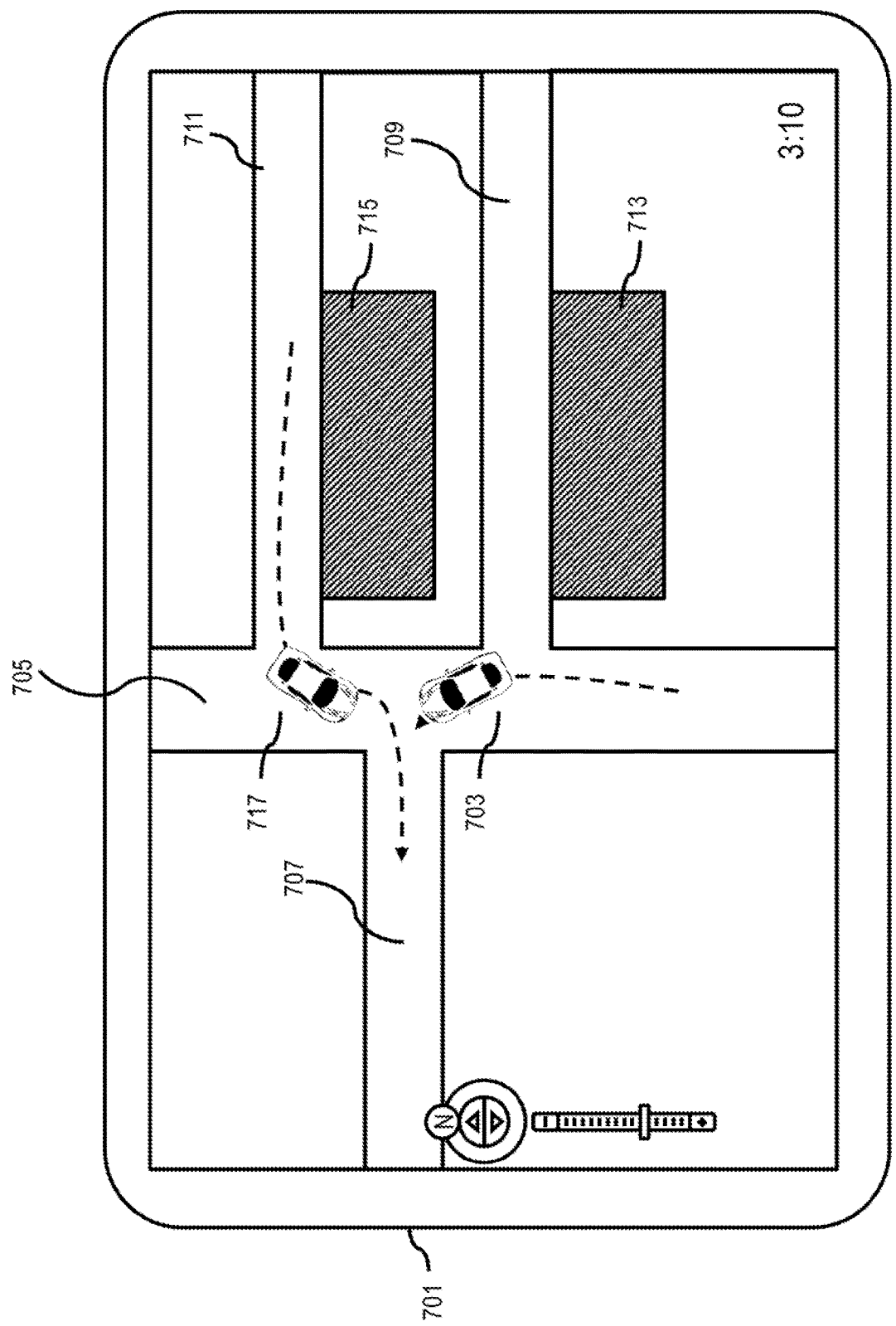
Figure 7D:
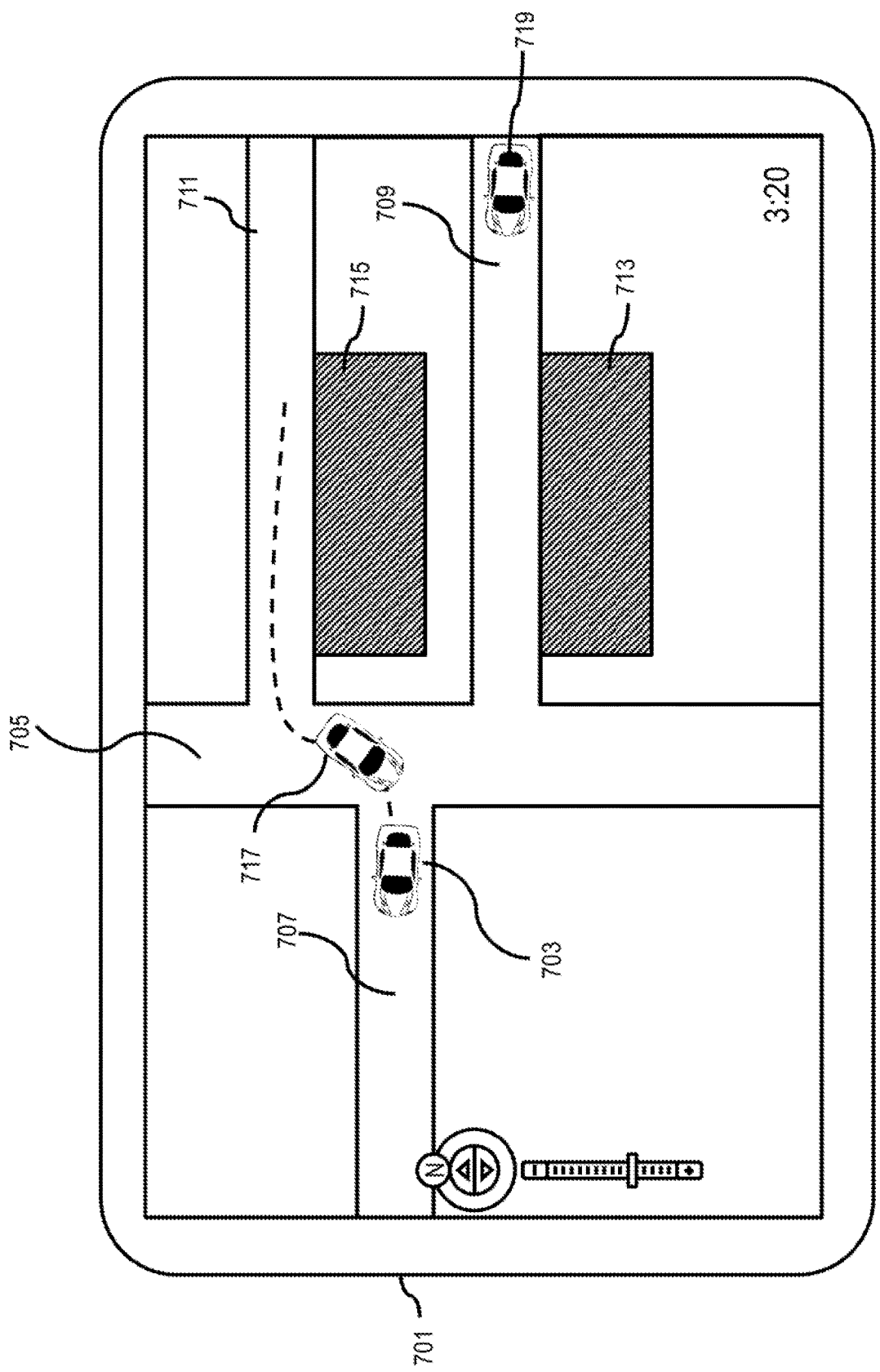

In one embodiment, the map user interface 701 may be used by a passenger (e.g., a front seat passenger) to control the presentation of the simulation (i.e., play the future or the past). By way of example, the front seat passenger could touch a section of the map user interface 701 to speed up or slow down the presentation of the simulation of the future event (i.e., "play with the time"). In one embodiment, the passenger may also tailor the presentation to her/his interests, for example, presenting only one object (e.g., vehicle 717); multiple objects (e.g., vehicles 717 and 719); all objects within a certain proximity; for a specific time (e.g., only between t3 and t4 when the visualization platform 107's confidence is at likely its highest); and/or based on a confidence level (e.g., only between t3 and t4). In one embodiment, the visualization platform 107 can enable a passenger to modify the operation of the vehicle 703 in response to the presented future event (e.g., by enabling the front seat passenger to interact with the map user interface 701). By way of example, the front seat passenger can touch or click on the vehicle 703 in FIG. 7C, for example, to indicate to the visualization platform 107 that the passenger does not feel confident coming face-to-face with vehicle 717 (i.e., she/he has had a negative reaction to the simulation of the future event) even though the visualization platform 107 has shown the passenger that the vehicles 703 and 717 will not collide in FIG. 7D. Consequently, the visualization platform 107 can cause the vehicle 703 to slow down or speed up—respecting of course all limitations and regulations (e.g., speed, traffic lights, etc.) to avoid the face-to-face event, as depicted in FIG. 7C. Likewise, the passenger can touch or click on the vehicle 703 in FIG. 7D to indicate to the visualization platform 107 that although she/he knows that there is sufficient time for vehicle 703 to turn before vehicle 717, she/he would prefer to allow the vehicle 717 to turn first (assuming that this would not dangerously impact traffic behind vehicle 703). Similarly, in one embodiment, the front seat passenger can "double click or tap", for example, the vehicle 703 in the map user interface 701 (e.g., in FIG. 7D) to alert the visualization platform 107 that the passenger is not worried/concerned about a specific vehicle/intersection/situation. In such an active mode, versus a passive mode wherein the visualization platform 107 simply computes and presents information to a passenger without allowing the passenger to "influence" some of the decisions coming in the next few seconds, the visualization platform 107 can quickly "move on" to the next set of computations relative to the vehicle 703 and the road 707.

FIGS. 8A-8D are diagrams illustrating a vehicle user interface depicting a simulated future event that is expected to occur proximate to a vehicle, according to one embodiment. As shown, the vehicle user interface 801 of FIGS. 8A-8D (e.g., a heads-up display or windshield) depicts a presentation of a future event over time t1 (FIG. 8A), t2 (FIG. 8B), t3 (FIG. 8C), and t4 (FIG. 8D), by the visualization platform 107 to one or more passengers of the vehicle 703 (e.g., an autonomous car). The use case of FIGS. 8A-8D generally follow the example described with respect to FIGS. 7A-7D, except in this instance, the visualization platform 107 simultaneously presents the future event as a 3D/AR view on the heads-up display or windshield 803 of the vehicle 703 and in the map user interface 701 of FIGS. 7A-7D (e.g., a 2D map), which in this instance is an integrated dashboard unit.

In this instance, the front seat passenger engages with the system 100 and controls the presentation of the simulated future event by turning the interface element 805 (e.g., a knob-based interface) to control and to manipulate the visualization of the simulated scene over time (i.e., "playing with the time"). By way of example, the passenger may want to initially view the simulated future event in a forward direction so that she/he may better understand and feel more confidence in the predicted future event and/or in the decisions of her/his vehicle 703. Thereafter, if they are still unclear about a maneuver or a timing of the maneuver, she/he may view the simulated future event in a reverse direction to get a better understanding and have more confidence in the vehicle 703's decisions. Consequently, the passenger first moves the interface element 805 to t1 (e.g., start) as shown by the indicator 807. In response to the passenger's interaction with the interface element 805, the visualization platform 107 can present the passenger with an AR view in the vehicle user interface 801 (e.g., a heads-up display) of the simulated future event including the passenger's vehicle 703 in its proximate position on the road 705 (e.g., at a starting time) and an "x-ray" view through buildings 713 and 715 of any oncoming traffic (e.g., vehicle 717 moving west on road 711) or objects of concern (e.g., pedestrians). In one example, the visualization platform 107 may acknowledge that the passenger understands that the vehicle 717 is approaching the same road 705 that she/he is traveling down (e.g., by detecting the passenger's gaze) and may then prompt the passenger to turn, e.g., the interface element 805 again to see the next sequence of the simulated future event.

Referring to FIG. 8B, once the passenger turns the interface element 805 to t2 (e.g., 5 seconds in the future) as shown by the indicator 809 and in the vehicle user interface 801 (e.g., +0:05), the visualization platform 107 can present the passenger with the simulated future event now showing the passenger's vehicle 703 in its proximate position on the road 705 and the proximate position of the vehicle 717, now much closer to the road 705. As discussed above, the visualization platform 107 may not have that much confidence in its predicted future event at t1 and t2 because the vehicle 717 is a moving object and appears to be driven by a human versus being another autonomous vehicle. As a result, the visualization platform 107 may represent the vehicle 717 at t1 and t2 in a color suggestive of warning or caution (e.g., yellow). In contrast, the visualization platform 107 may represent the passenger's vehicle 703 at t1 and t2 in a color suggestive of confidence and certainty (e.g., green or gold).

Once the passenger turns the interface element 805 to t3 (e.g., 10 seconds in the future) as shown by the indicator 811 and in the vehicle user interface 801 in FIG. 8C, the visualization platform 107 can present the proximate position of the passenger's vehicle 703 on the road 705 and the proximate position of the vehicle 717, now on the same road 705 and face-to-face. As discussed above, this portion of the predicted future event causes the passenger concern and discomfort (e.g., a detected from one or more sensors 115). At this time (t3), and now that the visualization platform 107 has collected and processed more contextual data, the visualization platform 107 can change the representation of the vehicle 717 to reflect an increased confidence level regarding the predicted future to make the passenger feel more confident in the vehicle 703's decisions and, therefore, potentially reduce the passenger's fear. For example, whereas the visualization platform 107 initially represented the vehicle 717 as yellow at t1 and t2 (FIGS. 8A and 8B, respectively), the visualization platform 107 can now represent the vehicle in green or gold or any color or manner suggestive of confidence or certainty. In one instance, because the visualization platform 107 can recognize that the passenger is most concerned about the predicted face-to-face encounter during t3 (e.g., based on an increase in the passenger's heart rate), the visualization platform 107 can prompt the passenger to continue viewing the simulated future event by turning the interface element 805 and/or the visualization platform 107 can automatically play the future for the passenger (e.g., if the visualization platform 107 determines that the passenger has a high level of concern or fear).

Referring to FIG. 8D, once the passenger turns the interface element 805 to t4 (e.g., 20 seconds in the future) as shown by the indicator 813 and in the vehicle user interface 801, the visualization platform 107 can present the proximate position of the passenger's vehicle 703, now on road 707 and well ahead of vehicle 717, and the proximate position of the vehicle 717, now just about to turn west from road 705 to road 707. Notably, the visualization platform 107 can present the simulated future event to the passenger in such a way that she/he may understand that there is sufficient distance between her/his vehicle 703 and the vehicle 717 so that she/he may have confidence in the decisions in the autonomous vehicle. As described above, in one instance, even if the visualization platform 107 represents high confidence in the simulated future event, the passenger may use the interface element 805 or touch or click on one of the vehicles to override the planned course and to allow the vehicle 717 to turn first, for example, if this would not cause a danger to vehicles behind vehicle 703. While FIGS. 8A-8D depict a forward representation of time, the passenger could also use the interface element 805 to move backwards in the simulated of the future event (e.g., to "replay" a scene that the passenger is uncertain about such as during t3).

The processes described herein for visualizing future events to a passenger of a vehicle may be advantageously implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 9:
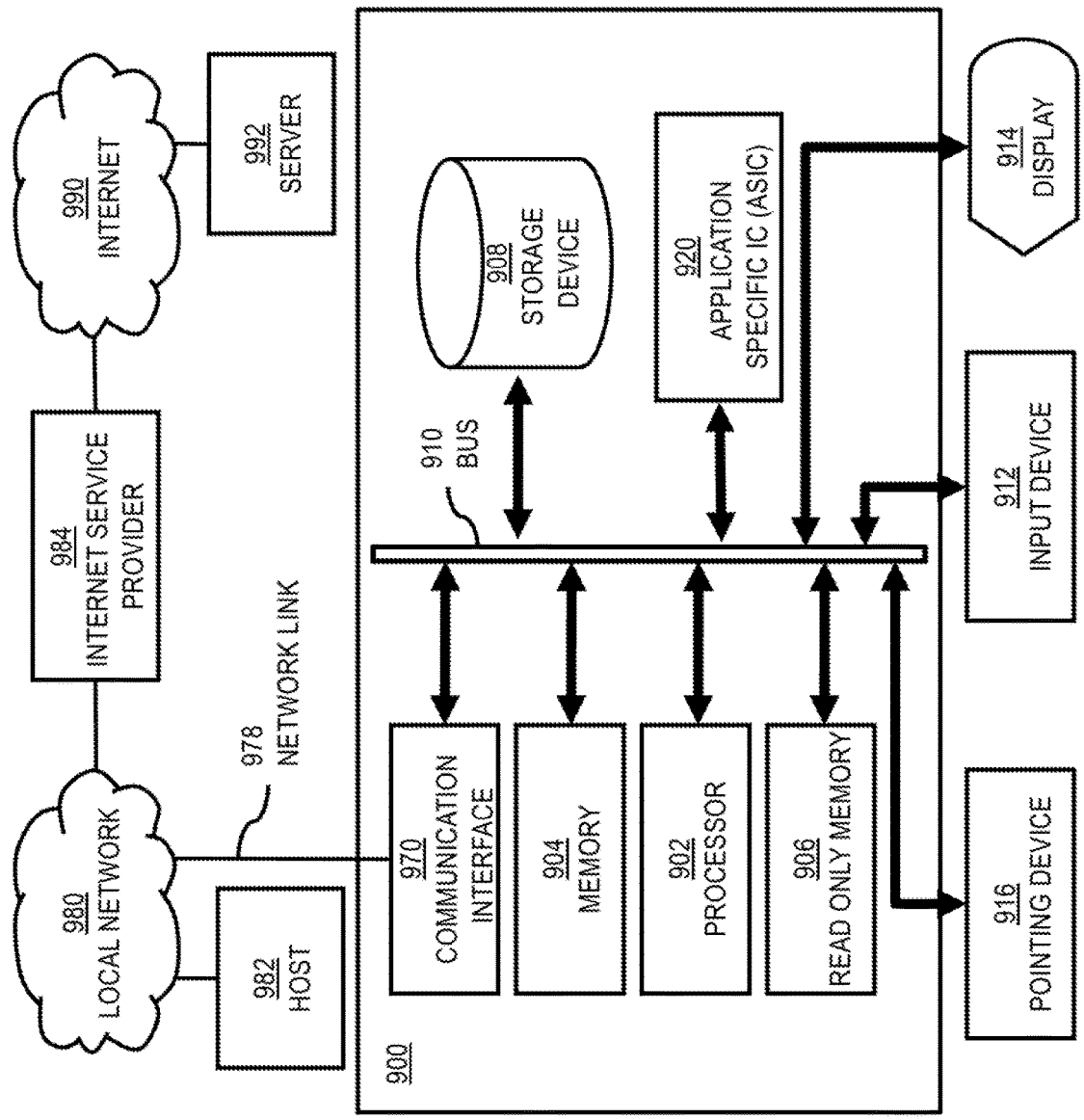
FIG. 9 is a diagram of hardware that can be used to implement an embodiment of the invention.

FIG. 9 illustrates a computer system 900 upon which an embodiment of the invention may be implemented. Computer system 900 is programmed (e.g., via computer program code or instructions) to visualize future events to a passenger of a vehicle as described herein and includes a communication mechanism such as a bus 910 for passing information between other internal and external components of the computer system 900. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range.

A bus 910 includes one or more parallel conductors of information so that information is transferred quickly among devices coupled to the bus 910. One or more processors 902 for processing information are coupled with the bus 910.

A processor 902 performs a set of operations on information as specified by computer program code related to visualizing future events to a passenger of a vehicle. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 910 and placing information on the bus 910.

The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 902, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 900 also includes a memory 904 coupled to bus 910. The memory 904, such as a random access memory (RAM) or other dynamic storage device, stores information including processor instructions for visualizing future events to a passenger of a vehicle. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of processor instructions. The computer system 900 also includes a read only memory (ROM) 906 or other static storage device coupled to the bus 910 for storing static information, including instructions, that is not changed by the computer system 900. Some memory is composed of volatile storage that loses the information stored thereon when power is lost. Also coupled to bus 910 is a non-volatile (persistent) storage device 908, such as a magnetic disk, optical disk or flash card, for storing information, including instructions, that persists even when the computer system 900 is turned off or otherwise loses power.

Information, including instructions for visualizing future events to a passenger of a vehicle, is provided to the bus 910 for use by the processor from an external input device 912, such as a keyboard containing alphanumeric keys operated by a human user, or a sensor. A sensor detects conditions in its vicinity and transforms those detections into physical expression compatible with the measurable phenomenon used to represent information in computer system 900. Other external devices coupled to bus 910, used primarily for interacting with humans, include a display device 914, such as a cathode ray tube (CRT) or a liquid crystal display (LCD), or plasma screen or printer for presenting text or images, and a pointing device 916, such as a mouse or a trackball or cursor direction keys, or motion sensor, for controlling a position of a small cursor image presented on the display 914 and issuing commands associated with graphical elements presented on the display 914. In some embodiments, for example, in embodiments in which the computer system 900 performs all functions automatically without human input, one or more of external input device 912, display device 914 and pointing device 916 is omitted.

In the illustrated embodiment, special purpose hardware, such as an application specific integrated circuit (ASIC) 920, is coupled to bus 910. The special purpose hardware is configured to perform operations not performed by processor 902 quickly enough for special purposes. Examples of application specific ICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a one-way or two-way communication coupling to a variety of external devices that operate with their own processors, such as printers, scanners and external disks. In general, the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. For wireless links, the communications interface 970 sends or receives or both sends and receives electrical, acoustic or electromagnetic signals, including infrared and optical signals, that carry information streams, such as digital data. For example, in wireless handheld devices, such as mobile telephones like cell phones, the communications interface 970 includes a radio band electromagnetic transmitter and receiver called a radio transceiver. In certain embodiments, the communications interface 970 enables connection to the communication network 109 for visualizing future events to a passenger of a vehicle.

The term non-transitory computer-readable medium is used herein to refer to any medium that participates in providing information to processor 902, including instructions for execution. Such a medium may take many forms, including, but not limited to, non-volatile media, volatile media and transmission media. Non-volatile or non-transitory media include, for example, optical or magnetic disks, such as storage device 908. Volatile media include, for example, dynamic memory 904. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read.

In one embodiment, a non-transitory computer-readable storage medium carrying one or more sequences of one or more instructions (e.g., computer code) which, when executed by one or more processors (e.g., a processor as described in any of FIGS. 9-11), cause an apparatus (e.g., the visualization platform 107, the vehicles 101, the UEs 105, etc.) to perform any steps of the various embodiments of the methods described herein.

FIG. 10 illustrates a chip set 1000 upon which an embodiment of the invention may be implemented. Chip set 1000 is programmed to visualize future events to a passenger of a vehicle as described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip.

In one embodiment, the chip set 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform the inventive steps described herein to visualize future events to a passenger of a vehicle. The memory 1005 also stores the data associated with or generated by the execution of the inventive steps.

Figure 11:
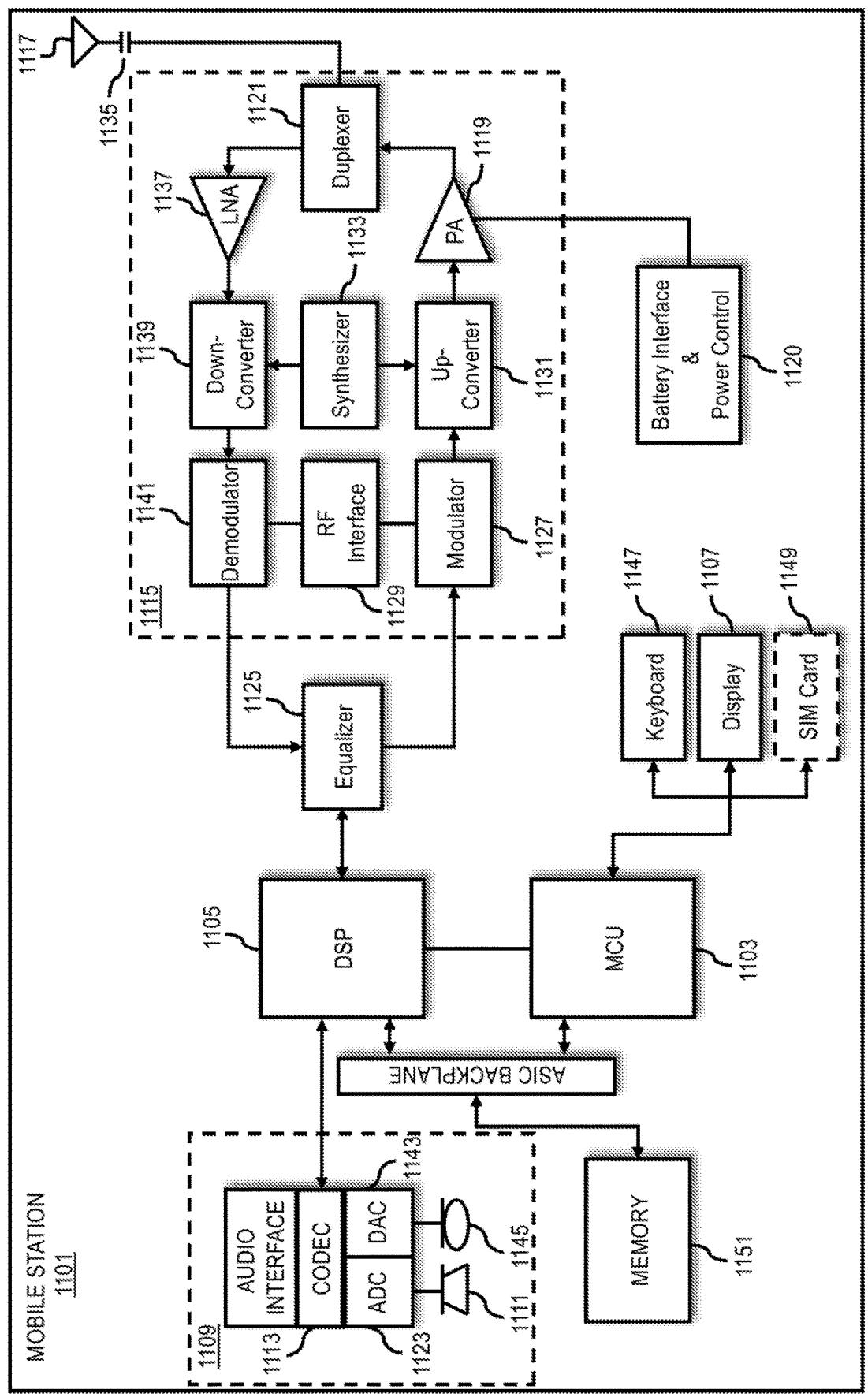
FIG. 11 is a diagram of a mobile terminal (e.g., handset) that can be used to implement an embodiment of the invention.

FIG. 11 is a diagram of exemplary components of a mobile station (e.g., handset) capable of operating in the system of FIG. 1, according to one embodiment. In one embodiment the mobile station can be the vehicle 101 or a component of the vehicle 101 configured to perform or more of the embodiments described herein. In another embodiment, the mobile station is an example of the UE 105 and can perform embodiments of the processes associated with functions of the UE 105. Generally, a radio receiver is often defined in terms of front-end and back-end characteristics. The front-end of the receiver encompasses all of the Radio Frequency (RF) circuitry whereas the back-end encompasses all of the base-band processing circuitry. Pertinent internal components of the telephone include a Main Control Unit (MCU) 1103, a Digital Signal Processor (DSP) 1105, and a receiver/transmitter unit including a microphone gain control unit and a speaker gain control unit. A main display unit 1107 provides a display to the user in support of various applications and mobile station functions that offer automatic contact matching. An audio function circuitry 1109 includes a microphone 1111 and microphone amplifier that amplifies the speech signal output from the microphone 1111. The amplified speech signal output from the microphone 1111 is fed to a coder/decoder (CODEC) 1113.

A radio section 1115 amplifies power and converts frequency in order to communicate with a base station, which is included in a mobile communication system, via antenna 1117. The power amplifier (PA) 1119 and the transmitter/modulation circuitry are operationally responsive to the MCU 1103, with an output from the PA 1119 coupled to the duplexer 1121 or circulator or antenna switch, as known in the art. The PA 1119 also couples to a battery interface and power control unit 1120.

In use, a user of mobile station 1101 speaks into the microphone 1111 and his or her voice along with any detected background noise is converted into an analog voltage. The analog voltage is then converted into a digital signal through the Analog to Digital Converter (ADC) 1123. The control unit 1103 routes the digital signal into the DSP 1105 for processing therein, such as speech encoding, channel encoding, encrypting, and interleaving. In one embodiment, the processed voice signals are encoded, by units not separately shown, using a cellular transmission protocol such as global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), WiFi, satellite, and the like.

The encoded signals are then routed to an equalizer 1125 for compensation of any frequency-dependent impairments that occur during transmission though the air such as phase and amplitude distortion. After equalizing the bit stream, the modulator 1127 combines the signal with a RF signal generated in the RF interface 1129. The modulator 1127 generates a sine wave by way of frequency or phase modulation. In order to prepare the signal for transmission, an up-converter 1131 combines the sine wave output from the modulator 1127 with another sine wave generated by a synthesizer 1133 to achieve the desired frequency of transmission. The signal is then sent through a PA 1119 to increase the signal to an appropriate power level. In practical systems, the PA 1119 acts as a variable gain amplifier whose gain is controlled by the DSP 1105 from information received from a network base station. The signal is then filtered within the duplexer 1121 and optionally sent to an antenna coupler 1135 to match impedances to provide maximum power transfer. Finally, the signal is transmitted via antenna 1117 to a local base station. An automatic gain control (AGC) can be supplied to control the gain of the final stages of the receiver. The signals may be forwarded from there to a remote telephone which may be another cellular telephone, other mobile phone or a land-line connected to a Public Switched Telephone Network (PSTN), or other telephony networks.

Voice signals transmitted to the mobile station 1101 are received via antenna 1117 and immediately amplified by a low noise amplifier (LNA) 1137. A down-converter 1139 lowers the carrier frequency while the demodulator 1141 strips away the RF leaving only a digital bit stream. The signal then goes through the equalizer 1125 and is processed by the DSP 1105. A Digital to Analog Converter (DAC) 1143 converts the signal and the resulting output is transmitted to the user through the speaker 1145, all under control of a Main Control Unit (MCU) 1103—which can be implemented as a Central Processing Unit (CPU) (not shown).

The MCU 1103 receives various signals including input signals from the keyboard 1147. The keyboard 1147 and/or the MCU 1103 in combination with other user input components (e.g., the microphone 1111) comprise a user interface circuitry for managing user input. The MCU 1103 runs a user interface software to facilitate user control of at least some functions of the mobile station 1101 to visualize future events to a passenger of a vehicle. The MCU 1103 also delivers a display command and a switch command to the display 1107 and to the speech output switching controller, respectively. Further, the MCU 1103 exchanges information with the DSP 1105 and can access an optionally incorporated SIM card 1149 and a memory 1151. In addition, the MCU 1103 executes various control functions required of the station. The DSP 1105 may, depending upon the implementation, perform any of a variety of conventional digital processing functions on the voice signals. Additionally, DSP 1105 determines the background noise level of the local environment from the signals detected by microphone 1111 and sets the gain of microphone 1111 to a level selected to compensate for the natural tendency of the user of the mobile station 1101.

The CODEC 1113 includes the ADC 1123 and DAC 1143. The memory 1151 stores various data including call incoming tone data and is capable of storing other data including music data received via, e.g., the global Internet. The software module could reside in RAM memory, flash memory, registers, or any other form of writable non-transitory computer readable storage medium known in the art. The memory device 1151 may be, but not limited to, a single memory, CD, DVD, ROM, RAM, EEPROM, optical storage, or any other non-volatile storage medium capable of storing digital data.

An optionally incorporated SIM card 1149 carries, for instance, important information, such as the cellular phone number, the carrier supplying service, subscription details, and security information. The SIM card 1149 serves primarily to identify the mobile station 1101 on a radio network. The card 1149 also contains a memory for storing a personal telephone number registry, text messages, and user specific mobile station settings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A computer-implemented method comprising:
    collecting, by one or more processors, sensor data, contextual data, or a combination thereof during an operation of a vehicle;
    processing, by the one or more processors, the sensor data, the contextual data, or a combination thereof to predict a future event that is expected to occur proximate to the vehicle, wherein the future event involves a change of context of at least one object external to the vehicle;
    generating a simulation of the future event; and
    before the future event occurs, performing, by the one or more processors, one or more of:
    (i) causing one or more displays to display the simulation of the future event in the vehicle,
    (ii) causing one or more speakers to output audio in the vehicle in accordance with the simulation of the future event, or
    (iii) causing one or more physical actuators in the vehicle to actuate in accordance with the simulation of the future event.

2. The method of claim 1, further comprising:
    determining that the object will be proximate to the vehicle based on a relevance level of the object to the user in the vehicle,
    wherein the change of the context of the object is presented via the one or more displays, the one or more speakers, the one or more physical actuators, or a combination thereof.

3. The method of claim 2, wherein the object is presented in the vehicle while physically located outside of a field of view of a user in the vehicle, and the future event includes an autonomous maneuver that the vehicle is predicted to take in response to the object, a predicted movement of the object, or a combination thereof.

4. The method of claim 2, wherein the relevance level of the object is determined based on sensor data indicating that the user is reacting to the object, and wherein the change of the context of the object includes a location change, a speed change, a direction change, a light change, a weather change, a visibility change, or a combination thereof.

5. The method of claim 4, wherein the sensor data is collected using at least one sensor configured to detect a gaze, a heartrate, a sweating rate, an eye movement, a body movement, or a combination thereof of the user.

6. The method of claim 1, wherein the one or more displays, the one or more speakers, the one or more physical actuators, or a combination thereof include at least one user interface element configured to receive a user input to specify at least one parameter of the simulation, and wherein the simulation is generated based on the at least one parameter, and wherein the at least one user interface element includes at least one knob, at least one joystick, at least one rollerball, at least one trackball-based interface, at least one touch screen, at least one microphone, or a combination thereof.

7. The method of claim 6, wherein the at least one parameter includes a time duration, a starting time, a time direction, or a combination thereof.

8. The method of claim 1, further comprising:
    determining a confidence level of the future event,
    wherein at least one characteristic of the simulation of the future event is presented based on the confidence level.

9. The method of claim 1, wherein the future event includes a plurality of potential outcomes, the method further comprising:
    presenting respective representations of at least two of the plurality of potential outcomes in the one or more displays, the one or more speakers, the one or more physical actuators, or a combination thereof,
    wherein the one or more displays include a vehicle windshield, a heads-up display, a handheld display, an integrated dashboard, a headrest display, a goggle, an eyeglass device, or a combination thereof.

10. The method of claim 1, wherein the one or more physical actuators actuate one or more physical sensations predicted in the simulation of the future event.

11. The method of claim 1, wherein the one or more displays, the one or more speakers, the one or more physical actuators, or a combination thereof include or communicate with at least one user interface element configured to receive a user input to modify the operation of the vehicle in response to the future event.

12. The method of claim 11, further comprising:
determining a negative reaction of the user to the simulation of the future event; and
modifying the operation of the vehicle to prevent the future event from happening, based on the negative reaction, the user input to modify the operation of the vehicle, or a combination thereof.

13. An apparatus comprising:
at least one processor; and
at least one memory including computer program code for one or more programs,
the at least one memory and the computer program code configured to, with the at least one processor, cause the apparatus to perform at least the following,
collect sensor data, contextual data, or a combination thereof during an operation of a vehicle;
process the sensor data, the contextual data, or a combination thereof to predict an event that is expected to occur proximate to the vehicle, wherein the event involves a change of context of at least one object external to the vehicle;
generate a simulation of the event; and
before the future event occurs, performing, by the one or more processors, one or more of the following:
(i) cause one or more displays to display the simulation of the future event in the vehicle,
(ii) cause one or more speakers to output audio in the vehicle in accordance with the simulation of the future event, or
(iii) cause one or more physical actuators in the vehicle to actuate in accordance with the simulation of the future event.

14. The apparatus of claim 13, wherein the one or more displays, the one or more speakers, the one or more physical actuators, or a combination thereof include or communicate with at least one user interface element configured to receive a user input to specify at least one parameter of the simulation, and wherein the simulation is generated based on the at least one parameter.

15. The apparatus of claim 13, wherein the apparatus is further caused to:
determine a confidence level of the future event,
wherein at least one characteristic of the simulation of the future event is presented based on the confidence level.

16. The apparatus of claim 13, wherein the future event includes a plurality of potential outcomes, the apparatus is further caused to:
present respective representations of at least two of the plurality of potential outcomes in the one or more displays, the one or more speakers, the one or more physical actuators, or a combination thereof.

17. A non-transitory computer-readable storage medium for generating vulnerable road user data for a geographic database, carrying one or more sequences of one or more instructions which, when executed by one or more processors, cause an apparatus to perform:
determining an object proximate to a vehicle based on a relevance level of the object to a user of the vehicle;
predicting a future event involving a change of context of the object based on sensor data, contextual data, or a combination, wherein the object is external to the vehicle;
generating a simulation of the future event; and
before the future event occurs, performing, by the one or more processors, one or more of the following:
(i) causing one or more displays to display the simulation of the future event in the vehicle,
(ii) causing one or more speakers to output audio in the vehicle in accordance with the simulation of the future event, or
(iii) causing one or more physical actuators in the vehicle to actuate in accordance with the simulation of the future event.

18. The non-transitory computer-readable storage medium of claim 17, wherein the apparatus is further caused to perform:
determining that the object will be proximate to the vehicle based on a relevance level of the object to the user in the vehicle,
wherein the change of the context of the object is presented in the one or more displays, the one or more speakers, the one or more physical actuators, or a combination thereof.

19. The non-transitory computer-readable storage medium of claim 18, wherein the relevance level of the object is determined based on sensor data indicating that the user is reacting to the object.

20. The non-transitory computer-readable storage medium of claim 17, wherein the apparatus is further caused to perform:
determining a confidence level of the future event,
wherein at least one characteristic of the simulation of the future event is presented based on the confidence level.

* * * * *